US010226407B2

(12) United States Patent
Nawrocki et al.

(10) Patent No.: US 10,226,407 B2
(45) Date of Patent: Mar. 12, 2019

(54) ORAL CARE COMPOSITIONS

(71) Applicant: COLGATE-PALMOLIVE COMPANY, New York, NY (US)

(72) Inventors: Shiri Nawrocki, Tenafly, NJ (US); Viktor Dubovoy, Cresskill, NJ (US); Long Pan, Somerset, NJ (US); Zhigang Hao, Bridgewater, NJ (US); Nihal Dogu, Dayton, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/393,953

(22) Filed: Dec. 29, 2016

(65) Prior Publication Data

US 2017/0231879 A1 Aug. 17, 2017

Related U.S. Application Data

(60) Provisional application No. 62/273,304, filed on Dec. 30, 2015.

(51) Int. Cl.
*A61K 8/19* (2006.01)
*A61K 8/24* (2006.01)
*A61Q 11/00* (2006.01)

(52) U.S. Cl.
CPC ............... *A61K 8/24* (2013.01); *A61K 8/19* (2013.01); *A61Q 11/00* (2013.01)

(58) Field of Classification Search
CPC .................................. A61K 8/30; A61K 8/21
USPC .............................................. 424/49, 50, 52
See application file for complete search history.

(56) References Cited

U.S. PATENT DOCUMENTS

| | | |
|---|---|---|
| 2,876,166 A | 3/1959 | Nebergall |
| 3,028,216 A | 4/1962 | Gemmell et al. |
| 4,071,615 A | 1/1978 | Barth |
| 4,198,394 A | 4/1980 | Faunce |
| 4,292,306 A | 9/1981 | Faunce |
| 4,340,583 A | 7/1982 | Wason |
| 4,350,680 A | 9/1982 | Harvey et al. |
| 4,627,977 A | 12/1986 | Gaffar et al. |
| 4,961,924 A | 10/1990 | Suhonen |
| 5,000,944 A | 3/1991 | Prencipe et al. |
| 5,004,597 A | 4/1991 | Majeti et al. |
| 5,017,363 A | 5/1991 | Suhonen |
| 5,145,666 A | 9/1992 | Lukacovic et al. |
| 5,188,820 A | 2/1993 | Cummins et al. |
| 5,213,790 A | 5/1993 | Lukacovic et al. |
| 5,258,173 A | 11/1993 | Waterfield |
| 5,281,410 A | 1/1994 | Lukacovic et al. |
| 5,281,411 A | 1/1994 | Majeti et al. |
| 5,338,537 A | 8/1994 | White, Jr. et al. |
| 5,487,906 A | 1/1996 | Dixit et al. |
| 5,578,293 A | 11/1996 | Prencipe et al. |
| 5,599,527 A | 2/1997 | Hsu et al. |
| 5,703,959 A | 12/1997 | Asano et al. |
| 5,716,600 A | 2/1998 | Zahradnik et al. |
| 5,939,051 A | 8/1999 | Santalucia et al. |
| 5,939,052 A | 8/1999 | White, Jr. et al. |
| 6,187,295 B1 | 2/2001 | Glandorf |
| 6,190,644 B1 | 2/2001 | McClanahan et al. |
| 6,350,436 B1 | 2/2002 | Glandorf et al. |
| 6,464,963 B1 | 10/2002 | Gambogi et al. |
| 6,555,094 B1 | 4/2003 | Glandorf et al. |
| 6,652,841 B1 | 11/2003 | Brown et al. |
| 6,685,920 B2 | 2/2004 | Baig et al. |
| 6,696,045 B2 | 2/2004 | Yue et al. |
| 6,713,049 B1 | 3/2004 | White, Jr. et al. |
| 6,740,311 B2 | 5/2004 | White, Jr. et al. |
| 6,821,507 B2 | 11/2004 | Glandorf et al. |
| 7,387,774 B2 | 6/2008 | Faller et al. |
| 8,211,409 B2 | 7/2012 | Baig et al. |
| 8,283,135 B2 | 10/2012 | Doyle et al. |
| 8,481,004 B2 | 7/2013 | Brown et al. |
| 8,628,755 B2 | 1/2014 | Prencipe |
| 8,906,347 B2 | 12/2014 | Strand et al. |
| 8,940,280 B2 | 1/2015 | Brown et al. |
| 8,956,593 B2 | 2/2015 | Burgess et al. |
| 9,017,647 B2 | 4/2015 | Midha et al. |
| 9,072,658 B2 | 7/2015 | Gadkari et al. |
| 9,139,731 B2 | 9/2015 | Baig et al. |
| 9,486,396 B2 | 11/2016 | Maloney et al. |
| 2005/0112070 A1 | 5/2005 | Glandorf et al. |
| 2007/0025928 A1 | 2/2007 | Glandorf et al. |
| 2007/0183989 A1 | 8/2007 | Prencipe et al. |
| 2008/0286214 A1 | 11/2008 | Brown et al. |
| 2011/0306018 A1 | 12/2011 | Doyle et al. |

(Continued)

FOREIGN PATENT DOCUMENTS

| | | |
|---|---|---|
| EP | 2 057 978 A1 | 5/2009 |
| EP | 2 289 482 A2 | 3/2011 |

(Continued)

OTHER PUBLICATIONS

Buchner, M. et al., "Pyrophosphate Complex of Tin(II) in Aqueous Solutions as Applied in Electrolytes for the Deposition of Tin and Tin Alloys Such as White Bronze," Inorganic Chemistry, 2012, 51, 8860-8867.

Crest Pro Health Toothpastes, 2 pages, retrieved Dec. 30, 2015, from http://www.pgsdscpsia.com/productsafety/ingredients/Crest_Pro_Health_Toothpastes.pdf.

Donaldson, J., "The Chemistry of Bivalent Tin," in Progress in Inorganic Chemistry, Cotton, F., Ed., 1967, John Wiley & Sons, Inc., pp. 287-356.

Safety Data Sheet for Crest Fro-Health Clean Cinnamon, face of document states Issuing Date: Apr. 2, 2015 and Revision Date: Apr. 2, 2015, 6 pages, retrieved Dec. 30, 2015, from: http://www.pg.com/productsafety/sds/SDS_2015/Crest%20Pro-Health%20Clean%20Cinnamon-95399027_RET_NG-2015040210392.pdf.

(Continued)

Primary Examiner — Walter E Webb

(57) ABSTRACT

Provided are aqueous soluble tin phosphate complexes formed from a mixture comprising tin (II) fluoride or tin (II) chloride and a tripolyphosphate salt, e.g., sodium tripolyphosphate ($Na_5P_3O_{10}$), and oral care compositions comprising the complex and uses thereof.

28 Claims, 7 Drawing Sheets

(56) References Cited

U.S. PATENT DOCUMENTS

| | | |
|---|---|---|
| 2012/0207686 A1 | 8/2012 | Fruge et al. |
| 2013/0017158 A1 | 1/2013 | Hoke, II et al. |
| 2013/0216485 A1 | 8/2013 | Campbell et al. |
| 2014/0086851 A1 | 3/2014 | Fisher et al. |
| 2016/0213581 A1 | 7/2016 | McGill |

FOREIGN PATENT DOCUMENTS

| | | |
|---|---|---|
| WO | WO 98/22079 A1 | 5/1998 |
| WO | WO 01/34108 A1 | 5/2001 |
| WO | WO 02/02128 A2 | 1/2002 |
| WO | WO 03/000217 A2 | 1/2003 |
| WO | WO 03/045344 A2 | 6/2003 |
| WO | WO 2004/054531 A1 | 7/2004 |
| WO | WO 2004/071321 A2 | 8/2004 |
| WO | WO 2007/062365 A2 | 5/2007 |
| WO | WO 2010/004361 | 1/2010 |
| WO | WO 2011/053291 A1 | 5/2011 |
| WO | WO 2012/060837 A1 | 5/2012 |
| WO | WO 2012/087288 A2 | 6/2012 |
| WO | WO 2012/166142 A1 | 12/2012 |
| WO | WO 2013/007018 A1 | 1/2013 |
| WO | WO 2013/033090 A1 | 3/2013 |
| WO | WO 2015/028096 A1 | 3/2015 |
| WO | WO 2015/195139 A1 | 12/2015 |
| WO | WO 2015/195140 A1 | 12/2015 |
| WO | WO 2016/178652 | 11/2016 |

OTHER PUBLICATIONS

Safety Data Sheet for Crest Pro-Health Clean Mint Toothpaste, face of document states Issuing Date: Apr. 2, 2015 and Revision Date: Aug. 13, 2015, 8 pages, retrieved Dec. 30, 2015, from http://www.pg.com/productsafety/sds/SDS_2015/SDS_Dec_2015/Crest_ProHealth_Clean_Mint_Toothpaste_95113822_RET_NG_2015081310209.pdf.

Safety Data Sheet for Crest Pro-Health for Life-Smooth Mint, face of document states: Issuing Date: Apr. 2, 2015 and Revistion Date: Apr. 2, 2015, 6 pages, retrieved Dec. 30, 2015, from http://www.pg.com/productsafety/sds/SDS_2015/Crest%20Pro-Health%20For%20Life-%20Smooth%20Mint-98941394_RET_NG-2015040291917.pdf.

Safety Data Sheet for Crest Pro-Health for Life-Smooth Mint, face of document states Issuing Date: Apr. 2, 2015 and Revision Date: Apr. 2, 2015, 6 pages, retrieved Dec. 30, 2015, from http://www.pg.com/productsafety/sds/SDS_2015/Crest%20Pro-Health%20For%20Life-%20Smooth%20Mint-98941394_RET_NG-2015040244324.pdf.

Safety Data Sheet for Crest Pro-Health Clean Mint Toothpaste, face of document states Issuing Date: Apr. 2, 2015 and Revision Date: Apr. 2, 2015, 6 pages, retrieved Dec. 30, 2015, from http://www.pg.com/productsafety/sds/SDS_2015/Crest%20Pro-Health%20Clean%20Mint%20Toothpaste-95113822_RET_NG-2015040210190.pdf.

Safety Data Sheet for Crest Pro-Health Intensive Clean—Cool Mint, face of document states Issuing Date: Apr. 2, 2015 and Revision Date: Apr. 2, 2015, 6 pages, retrieved Dec. 30, 2015, from http://www.pg.com/productsafety/sds/SDS_2015/Crest%20Pro-Health%20Intensive%20Clean%20-%20Cool%20Mint-95720693_RET_NG-201504029280.pdf.

Safety Data Sheet for Crest Pro-Health Intensive Clean—Cool Mint, face of document states Issuing Date: Apr. 2, 2015 and Revision Date: Jun. 29, 2015, 8 pages, retrieved Dec. 30, 2015, from http://www.pg.com/productsafety/sds/SDS_2015/SDS_Dec_2015/Crest_ProHealth_Intensive_Clean_Cool_Mint_95720693_RET_NG_2015102211039.pdf.

Safety Data Sheet for Crest Pro-Health Intensive Clean—Cool Mint, face of document states Issuing Date: Apr. 2, 2015 and Revision Date: Apr. 2, 2015, 6 pages, retrieved Dec. 30, 2015, from http://www.pg.com/productsafety/sds/SDS_2015/Crest%20Pro-Health%20Intensive%20Clean%20-%20Cool%20Mint-95720693_RET_NG-2015040272630.pdf.

Safety Data Sheet for Crest Pro-Health Whitening—Fresh Clean Mint, face of dcoument states Issuing Date: Apr. 8, 2015 and Revision Date: Apr. 8, 2015, 7 pages, retrieved Dec. 30, 2015, from http://www.pg.com/productsafety/sds/SDS_2015/Crest%20Pro-Health%20Whitening%20-Fresh%20Clean%20Mint-98543475_RET_NG-2015040845158.pdf.

Safety Data Sheet for Crest Pro-Health Healthy Fresh—Cool Peppermint, face of document states Issuing Date: Apr. 2, 2015 and Revision Date: Apr. 2, 2015, 6 pages, retrieved Dec. 30, 2015, from http://www.pg.com/productsafety/sds/SDS_2015/Crest%20Pro-Health%20Healthy%20Fresh-%20Cool%20Peppermint-92090509_RET_NG-20150402750.pdf.

Safety Data Sheet for Crest Pro-Health Healthy Fresh—Cool Peppermint, face of document states Issuing Date: Apr. 2, 2015 and Revision Date: Apr. 2, 2015, 6 pages, retrieved Dec. 30, 2015, from http://www.pg.com/productsafety/sds/SDS_2015/Crest%20Pro-Health%20Healthy%20Fresh-%20Cool%20Peppermint-92090509_RET_NG-2015040292539.pdf.

Safety Data Sheet for Crest Pro-Health Clinical Plaque Control—Fresh Mint, face of document states Issuing Date: No data available and Revision Date: Aug. 13, 2015, 8 pages, retrieved Dec. 30, 2015, from http://www.pg.com/productsafety/sds/SDS_2015/SDS_Dec_2015/Crest_ProHealth-Clinical_Plaque_Control_Fresh_Mint_99867882_RET_NG_2015081311225.pdf.

Safety Data Sheet for Crest Pro-Health Sensitive + Enamel Sheild—Smooth Mint, face of document states Issuing Date: Apr. 2, 2015 and Revision Date: Apr. 2, 2015, 6 pages, retrieved Dec. 30, 2015, from http://www.pg.com/productsafety/sds/SDS_2015/Crest%20Pro-Health%20Sensitive%20+%20Enamel%20Sheild-%20Smooth%20Mint-95931348_RET_NG-201504029300.pdf.

Safety Data Sheet for Crest Pro-Health Clinical Plaque Control—Fresh Mint, face of document states Issuing Date: No data available and Revision Date: Apr. 2, 2015, 6 pages, retrieved Dec. 30, 2015, from http://www.pg.com/productsafety/sds/SDS_2015/Crest%20Pro-Health%20Clinical%20Plaque%20Control%20-%20Fresh%20Mint-99867882_RET_NG-2015040295522.pdf.

Safety Data Sheet for Crest Pro-Health Sensitive + Enamel Sheild—Smooth Mint, face of document states Issuing Date: Apr. 2, 2015 and Revision Date: Apr. 2, 2015, 6 pages, retrieved Dec. 30, 2015, from http://www.pg.com/productsafety/sds/SDS_2015/Crest%20Pro-Health%20Sensitive%20+%20Enamel%20Sheild-%20Smooth%20Mint-95931348_RET_NG-2015040210328.pdf.

Safety Data Sheet for Crest Pro-Health Clinical Gum Protection—Soothing Smooth Mint, face of document states Issuing Date: Apr. 2, 2015 and Revision Date: Apr. 2, 2015, 7 pages, retrieved Dec. 30, 2015, from http://www.pg.com/productsafety/sds/SDS_2015/Crest%20Pro-Health%20Clinical%20Gum%20Protection%20-%20Soothing%20Smooth%20Mint-98854209_RET_NG-201504029519.pdf.

Safety Data Sheet for Crest Pro-Health Clinical Gum Protection—Soothing Smooth Mint, face of document states Issuing Date: Apr. 2, 2015 and Revision Date: Aug. 13, 2015, 8 pages, retrieved Dec. 30, 2015, from http://www.pg.com/productsafety/sds/SDS_2015/SDS_Dec_2015/Crest_ProHealth_Clinical_Gum_Protection_Soothing_Smooth_Mint_98854209_RET_NG_20150813113638.pdf.

Safety Data Sheet for Crest Pro-Health Clinical Gum Protection—Invigorating Clean Mint, face of document states Issuing Date: No data available and Revision Date: Aug. 13, 2015, 8 pages, retrieved Dec. 30, 2015, from http://www.pg.com/productsafety/sds/SDS_2015/SDS_Dec_2015/Crest_ProHealth_Clinical_Gum_Protection_Invigorating_Clean_Mint_99543035_RET_NG_20150813114619.pdf.

Safety Data Sheet for Crest Pro-Health [HD] Step 1 Fluoride Toothpaste for Anti-Cavity and Anti-Gingivitis, face of document states Issuing Date: Apr. 14, 2015 and Revision Date: Apr. 14, 2015, 6 pages, retrieved Dec. 30, 2015, from http://www.pg.com/productsafety/sds/SDS_2015/Crest%20Pro-Health%20%5BHD%5D%20Step%201%20Fluoride%20Toothpaste%20for%20Anti-Cavity%20and%20Anti-Gigivitis-97263583_RET_NG-201504146928.pdf.

(56) References Cited

OTHER PUBLICATIONS

International Search Report and Written Opinion of the International Searching Authority in International Application No. PCT/US2016/069178, dated Feb. 24, 2017.

ORAL CARE COMPOSITIONS

This application claims priority to U.S. Provisional Application No. 62/273,304 filed Dec. 30, 2015, which is hereby incorporated by reference in its entirety.

BACKGROUND

Dentinal hypersensitivity is acute, localized tooth pain in response to physical stimulation of the dentine surface by thermal (hot or cold), osmotic, tactile, and/or a combination of thermal, osmotic, and tactile stimulation of the exposed dentin. Exposure of the dentine, which is generally due to recession of the gums, or loss of enamel, frequently leads to hypersensitivity. Dentinal tubules open to the surface have a high correlation with dentinal hypersensitivity. Dentinal tubules lead from the pulp to the cementum. When the surface cementum of the tooth root is eroded, the dentinal tubules become exposed to the external environment. The exposed dentinal tubules provide a pathway for transmission of fluid flow to the pulpal nerves, the transmission induced by changes in temperature, pressure, and ionic gradients.

To relieve dentinal hypersensitivity, dentinal tubules may be plugged. Such occlusion may be carried out either by blocking the tubule with a particle of smaller size than the tubule or by inducing precipitation within the dentin tubule itself.

Tin (II) fluoride (also known as stannous fluoride, $SnF_2$) has been used in oral care compositions, but has disadvantages. Tin (II) may react with other ingredients of the oral care composition to form insoluble inactive tin compounds, thereby reducing the effective amount of available tin (II) in the composition. In addition, tin (II) fluoride may cause yellow-brown tooth staining and may impart unacceptable astringency to the composition.

While the prior art discloses the use of various oral compositions for the treatment of dentinal hypersensitivity, there is still a need for additional compositions and methods that provide improved performance in such treatments.

BRIEF SUMMARY

Tin (II) fluoride is soluble in water, however, it oxidizes to form insoluble precipitates of tin. In addition, tin can form water insoluble compounds with phosphates.

It has now been discovered that tin (II) fluoride and tin (II) chloride form aqueous soluble tin phosphate complexes upon mixture with a tripolyphosphate salt, e.g., an alkali tripolyphosphate salt, e.g., potassium tripolyphosphate ($K_5P_3O_{10}$) or sodium tripolyphosphate ($Na_5P_3O_{10}$) (STPP).

When the complexes are placed in an oral care composition, the oral care composition, upon use, may provide a precipitate that can plug dentinal tubules, thereby reducing the sensitivity of the teeth. While providing efficient delivery of tin in comparison to compositions with insoluble tin salts, the compositions comprising the tin phosphate complexes may not exhibit the instability, tooth staining, and poor taste associated with conventional tin-based oral care products using soluble tin salts.

Provided are aqueous soluble tin phosphate complexes, e.g., formed from a mixture comprising tin (II) fluoride or tin (II) chloride and a tripolyphosphate salt, e.g., an alkali tripolyphosphate salt, e.g., potassium tripolyphosphate ($K_5P_3O_{10}$) or sodium tripolyphosphate ($Na_5P_3O_{10}$), e.g., sodium tripolyphosphate ($Na_5P_3O_{10}$).

Also provided are oral care compositions, e.g., mouthwashes, oral gels, or dentifrices, comprising the aqueous soluble tin phosphate complexes. The compositions may be formulated in a suitable oral care composition, e.g., a mouthwash, oral gel, or dentifrice, for example comprising one or more abrasives, surfactants, foaming agents, vitamins, enzymes, humectants, thickeners, antimicrobial agents, whitening agents, pH agents, preservatives, flavorings, and/or colorants.

Further provided are mouthwashes comprising the aqueous soluble tin phosphate complexes, which are clear when formulated, but which provide a precipitate when contacted with saliva.

Further provided are methods of using the oral care compositions to reduce or inhibit dentinal hypersensitivity comprising applying the composition to teeth.

Further provided is a method of occluding dentin tubules comprising applying the oral care compositions to teeth.

Further provided are methods of using the oral care compositions to reduce or inhibit one or more of dental caries (i.e., cavities), gingivitis, and plaque comprising applying the composition to teeth.

Further provided are methods of making the aqueous soluble tin phosphate complexes comprising combining tin (II) fluoride or tin (II) chloride and a tripolyphosphate salt, e.g., an alkali tripolyphosphate salt, e.g., sodium tripolyphosphate, in aqueous solution, e.g., at a molar ratio of 1P:1Sn to less than 15P:1Sn, e.g., greater than 1P:1Sn to less than 15P:1Sn, e.g., 2P 1Sn to less than 15P:1Sn, e.g., 2P:1Sn to 10P:1Sn, e.g., 2P:1Sn to 5P:1Sn; optionally isolating the complexes thus formed as a solid.

Further provided are methods of making the oral care compositions comprising admixing the aqueous soluble tin phosphate complexes with an oral care base, e.g., a mouthwash, oral gel, or dentifrice base.

Further areas of applicability of the present invention will become apparent from the detailed description provided hereinafter. It should be understood that the detailed description and specific examples, while indicating preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Provided is an aqueous soluble tin phosphate complex (Complex 1), e.g., 1.1 Complex 1, wherein the complex is formed from a mixture comprising tin (II) fluoride and a tripolyphosphate salt, e.g., an alkali tripolyphosphate salt, e.g., potassium tripolyphosphate ($K_5P_3O_{10}$) or sodium tripolyphosphate ($Na_5P_3O_{10}$).

1.2 Complex 1, wherein the complex is formed from a mixture comprising tin (II) chloride and a tripolyphosphate salt, e.g., an alkali tripolyphosphate salt, e.g., potassium tripolyphosphate ($K_5P_3O_{10}$) or sodium tripolyphosphate ($Na_5P_3O_{10}$).

1.3 Complex 1 or 1.1, wherein the complex is formed from a mixture comprising tin (II) fluoride and a tripolyphosphate salt, e.g., an alkali tripolyphosphate salt, e.g., potassium tripolyphosphate ($K_5P_3O_{10}$) or sodium tripolyphosphate ($Na_5P_3O_{10}$), in an aqueous solution.

1.4 Complex 1 or 1.2 wherein the complex is formed from a mixture comprising tin (II) chloride and a tripolyphosphate salt, e.g., an alkali tripolyphosphate salt, e.g., potassium tripolyphosphate ($K_5P_3O_{10}$) or sodium tripolyphosphate ($Na_5P_3O_{10}$), in an aqueous solution.

1.5 Complex 1.3, wherein the aqueous solution has a pH from 4-9, e.g., from 5-8, e.g., from 5-7, e.g., from 5-6, e.g., from 6-8, e.g., from 6-7, e.g., from 7-8.

1.6 Complex 1.4, wherein the aqueous solution has a pH from 4-9, e.g., from 4-8, e.g., from 4-7, e.g., from 5-8, e.g., from 6-8, e.g., from 5-7, e.g., from 4-6, e.g., from 4-5, e.g., from 5-6, e.g., from 6-7, e.g., from 7-8.

1.7 Any of Complexes 1, 1.1, 1.3, or 1.5, wherein the complex is formed from a mixture comprising tin (II) fluoride and sodium tripolyphosphate ($Na_5P_3O_{10}$).

1.8 Any of Complexes 1, 1.2, 1.4, or 1.6, wherein the complex is formed from a mixture comprising tin (II) chloride and sodium tripolyphosphate ($Na_5P_3O_{10}$).

Figure 1:
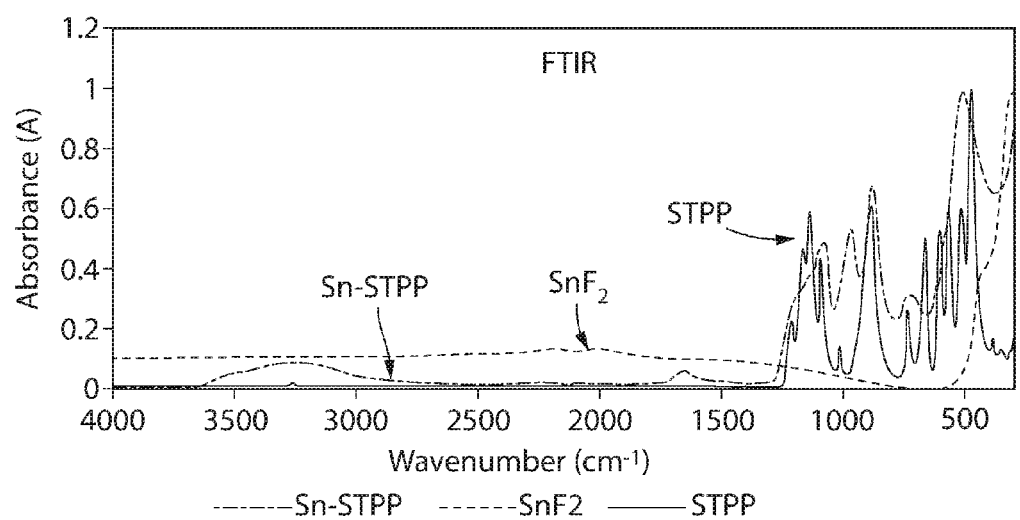
FIG. 1 depicts Fourier transform infrared spectra.

1.9 Any of the foregoing complexes, wherein the complex exhibits a Fourier transform infrared spectrum substantially as shown in the Sn-STPP spectrum in FIG. 1.

Figure 2:
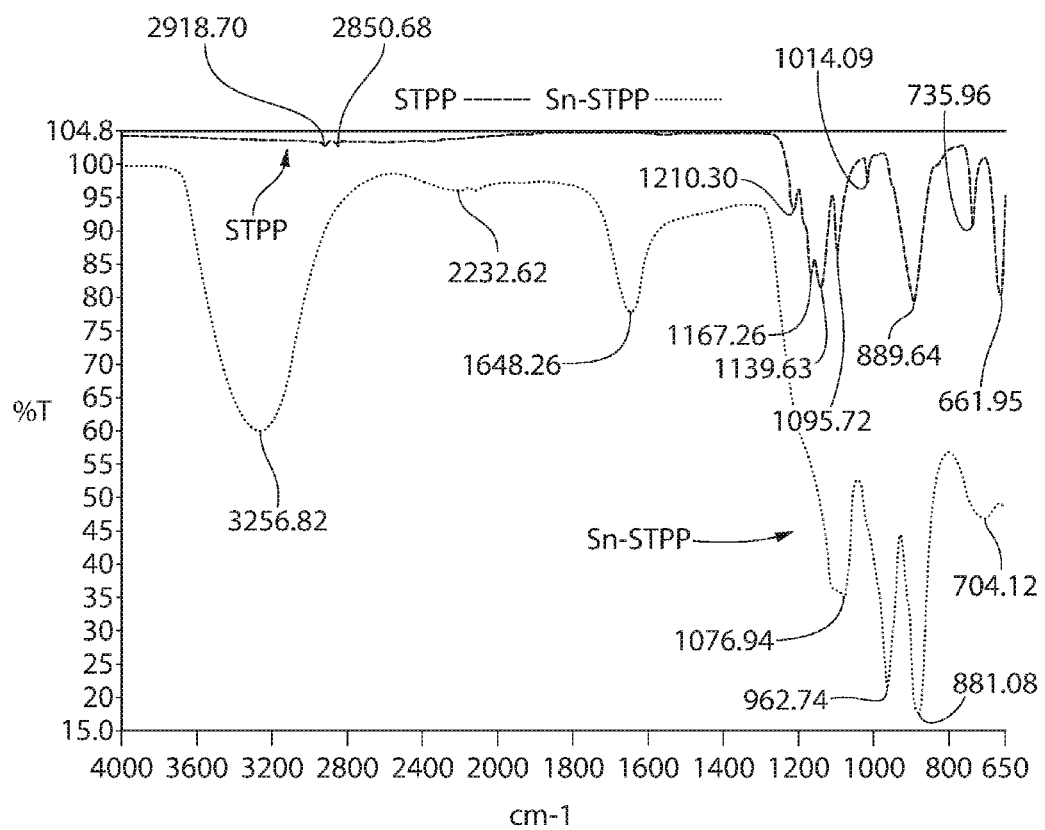
FIG. 2 depicts Fourier transform infrared spectra.

1.10 Any of the foregoing complexes, wherein the complex exhibits a Fourier transform infrared spectrum substantially as shown in the Sn-STPP spectrum in FIG. 2.

1.11 Any of the foregoing complexes, wherein the complex exhibits a Fourier transform infrared spectrum comprising one or more peaks selected from the group consisting of: 1077 $cm^{-1}$, 963 $cm^{-1}$, 881 $cm^{-1}$, and 704 $cm^{-1}$.

1.12 Any of the foregoing complexes, wherein the complex exhibits a Fourier transform infrared spectrum comprising one or more peaks selected from the group consisting of: 2233 $cm^{-1}$, 1077 $cm^{-1}$, 963 $cm^{-1}$, 881 $cm^{-1}$, and 704 $cm^{-1}$.

1.13 Any of the foregoing complexes, wherein the complex exhibits a Fourier transform infrared spectrum comprising one or more peaks selected from the group consisting of: 3257 $cm^{-1}$, 2233 $cm^{-1}$, 1648 $cm^{-1}$, 1077 $cm^{-1}$, 963 $cm^{-1}$, 881 $cm^{-1}$, and 704 $cm^{-1}$.

1.14 Any of the foregoing complexes, wherein the complex exhibits a Fourier transform infrared spectrum comprising the following peaks: 1077 $cm^{-1}$, 963 $cm^{-1}$, 881 $cm^{-1}$, and 704 $cm^{-1}$.

1.15 Any of the foregoing complexes, wherein the complex exhibits a Fourier transform infrared spectrum comprising the following peaks: 3257 $cm^{-1}$, 1648 $cm^{-1}$, 1077 $cm^{-1}$, 963 $cm^{-1}$, 881 $cm^{-1}$, and 704 $cm^{-1}$.

1.16 Any of the foregoing complexes, wherein the complex exhibits a Fourier transform infrared spectrum comprising the following peaks: 2233 $cm^{-1}$, 1077 $cm^{-1}$, 963 $cm^{-1}$, 881 $cm^{-1}$, and 704 $cm^{-1}$ 1.17 Any of the foregoing complexes, wherein the complex exhibits a Fourier transform infrared spectrum comprising the following peaks: 3257 $cm^{-1}$, 2233 $cm^{-1}$, 1648 $cm^{-1}$, 1077 $cm^{-1}$, 963 $cm^{-1}$, 881 $cm^{-1}$, and 704 $cm^{-1}$.

1.18 Any of the foregoing complexes, wherein the complex exhibits a Fourier transform infrared spectrum comprising one or more peaks selected from the group consisting of: 1081 $cm^{-1}$, 969 $cm^{-1}$, 883 $cm^{-1}$, 733 $cm^{-1}$, and 512 $cm^{-1}$.

Figure 3:
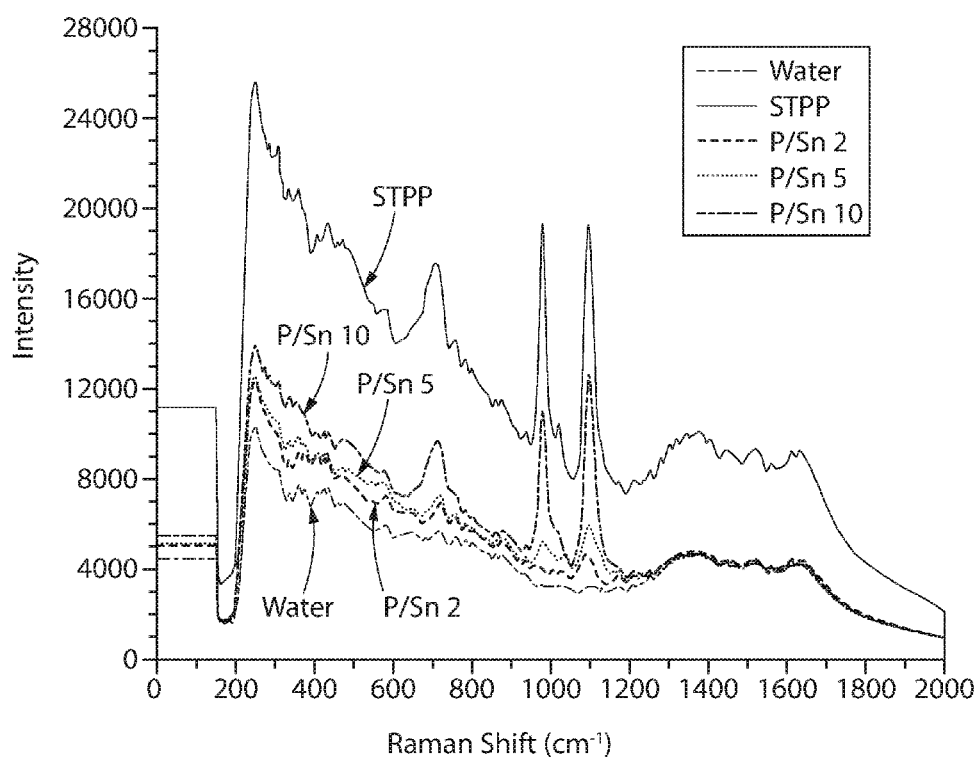
FIG. 3 depicts Raman spectra of water, STPP, and solutions with P:Sn molar ratios of 2, 5, and 10 (from top to bottom: STPP, P:Sn molar ratio 10, P:Sn molar ratio 5, P:Sn molar ratio 2, and water).

1.19 Any of the foregoing complexes, wherein the complex exhibits a Fourier transform infrared spectrum comprising the following peaks: 1081 $cm^{-1}$, 969 $cm^{-1}$, 883 $cm^{-1}$, 733 $cm^{-1}$, and 512 $cm^{-1}$ 1.20 Any of the foregoing complexes, wherein the complex exhibits a Raman spectrum substantially as shown in any of the P/Sn Raman spectra of FIG. 3.

1.21 Any of the foregoing complexes, wherein the complex exhibits a Raman spectrum comprising one or more peaks selected from the group consisting of: 719 $cm^{-1}$ and 1084 $cm^{-1}$ 1.22 Any of the foregoing complexes, wherein the complex exhibits a Raman spectrum comprising the following peaks: 719 $cm^{-1}$ and 1084 $cm^{-1}$ 1.23 Any of the foregoing complexes, wherein the complex exhibits a Raman spectrum comprising one or more peaks selected from the group consisting of: 719 $cm^{-1}$, 978 $cm^{-1}$, and 1084 $cm^{-1}$ 1.24 Any of the foregoing complexes, wherein the complex exhibits a Raman spectrum comprising the following peaks: 719 $cm^{-1}$, 978 $cm^{-1}$, and 1084 $cm^{-1}$.

1.25 Any of the foregoing complexes, wherein the complex exhibits a Raman spectrum comprising one or more peaks selected from the group consisting of: 712 $cm^{-1}$, 978 $cm^{-1}$, and 1094 $cm^{-1}$ 1.26 Any of the foregoing complexes, wherein the complex exhibits a Raman spectrum comprising the following peaks: 712 $cm^{-1}$, 978 $cm^{-1}$, and 1094 $cm^{-1}$.

Figure 4:
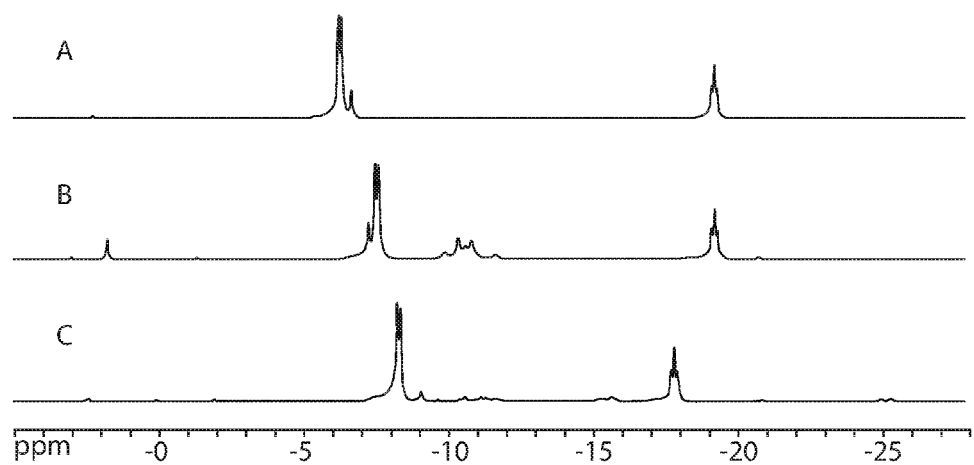
FIG. 4 depicts $^{31}P$ NMR spectra of solutions with P:Sn molar ratios of 10 (A), 5 (B), and 2 (C).

1.27 Any of the foregoing complexes, wherein the complex exhibits a $^{31}P$ NMR spectrum as shown in any of the NMR spectra of FIG. 4, A, 4, B, or 4, C, wherein the NMR spectrum is obtained on an aqueous solution with 5 weight % $D_2O$ added and is externally referenced to 85% $H_3PO_4$ set to 0 ppm.

1.28 Any of the foregoing complexes, wherein the complex exhibits a $^{31}P$ NMR spectrum comprising one or more peaks selected from the group consisting of: −6 ppm (doublet) and −19 ppm (triplet), e.g., −6.2 ppm (doublet), −6.3 ppm (doublet), −19.1 ppm (triplet), −19.2 ppm (triplet), and −19.3 ppm (triplet), e.g., −6.24 ppm (doublet), −6.33 ppm (doublet), −19.08 ppm (triplet), −19.17 ppm (triplet), and −19.27 ppm (triplet), wherein the NMR spectrum is obtained on an aqueous solution with 5 weight % $D_2O$ added and is externally referenced to 85% $H_3PO_4$ set to 0 ppm.

1.29 Any of the foregoing complexes, wherein the complex exhibits a $^{31}$P NMR spectrum comprising the following peaks: −6 ppm (doublet) and −19 ppm (triplet), e.g., −6.2 ppm (doublet), −6.3 ppm (doublet), −19.1 ppm (triplet), −19.2 ppm (triplet), and −19.3 ppm (triplet), e.g., −6.24 ppm (doublet), −6.33 ppm (doublet), −19.08 ppm (triplet), −19.17 ppm (triplet), and −19.27 ppm (triplet), wherein the NMR spectrum is obtained on an aqueous solution with 5 weight % D$_2$O added and is externally referenced to 85% H$_3$PO$_4$ set to 0 ppm.

1.30 Any of the foregoing complexes, wherein the complex exhibits a $^{31}$P NMR spectrum comprising one or more peaks selected from the group consisting of: 2 ppm, −6 ppm (doublet), −7 ppm, and −19 ppm (triplet), e.g., 2.2 ppm, −6.2 ppm (doublet), −6.3 ppm (doublet), −6.7 ppm, −19.1 ppm (triplet), −19.2 ppm (triplet), and −19.3 ppm (triplet), e.g., 2.21 ppm, −6.24 ppm (doublet), −6.33 ppm (doublet), −6.68 ppm, −19.08 ppm (triplet), −19.17 ppm (triplet), and −19.27 ppm (triplet), wherein the NMR spectrum is obtained on an aqueous solution with 5 weight % D$_2$O added and is externally referenced to 85% H$_3$PO$_4$ set to 0 ppm.

1.31 Any of the foregoing complexes, wherein the complex exhibits a $^{31}$P NMR spectrum comprising the following peaks: 2 ppm, −6 ppm (doublet), −7 ppm, and −19 ppm (triplet), e.g., 2.2 ppm, −6.2 ppm (doublet), −6.3 ppm (doublet), −6.7 ppm, −19.1 ppm (triplet), −19.2 ppm (triplet), and −19.3 ppm (triplet), e.g., 2.21 ppm, −6.24 ppm (doublet), −6.33 ppm (doublet), −6.68 ppm, −19.08 ppm (triplet), −19.17 ppm (triplet), and −19.27 ppm (triplet), wherein the NMR spectrum is obtained on an aqueous solution with 5 weight % D$_2$O added and is externally referenced to 85% H$_3$PO$_4$ set to 0 ppm.

1.32 Any of the foregoing complexes, wherein the complex exhibits a $^{31}$P NMR spectrum comprising one or more peaks selected from the group consisting of: −8 ppm (doublet) and −19 ppm (triplet), e.g., −7.5 ppm (doublet), −7.6 ppm (doublet), −19.1 ppm (triplet), −19.2 ppm (triplet), and −19.3 ppm (triplet), e.g., −7.52 ppm (doublet), −7.62 ppm (doublet), −19.09 ppm (triplet), −19.19 ppm (triplet), and −19.29 ppm (triplet), wherein the NMR spectrum is obtained on an aqueous solution with 5 weight % D$_2$O added and is externally referenced to 85% H$_3$PO$_4$ set to 0 ppm.

1.33 Any of the foregoing complexes, wherein the complex exhibits a $^{31}$P NMR spectrum comprising the following peaks: −8 ppm (doublet) and −19 ppm (triplet), e.g., −7.5 ppm (doublet), −7.6 ppm (doublet), −19.1 ppm (triplet), −19.2 ppm (triplet), and −19.3 ppm (triplet), e.g., −7.52 ppm (doublet), −7.62 ppm (doublet), −19.09 ppm (triplet), −19.19 ppm (triplet), and −19.29 ppm (triplet), wherein the NMR spectrum is obtained on an aqueous solution with 5 weight % D$_2$O added and is externally referenced to 85% H$_3$PO$_4$ set to 0 ppm.

1.34 Any of the foregoing complexes, wherein the complex exhibits a $^{31}$P NMR spectrum comprising one or more peaks selected from the group consisting of: 2 ppm, −7 ppm, −8 ppm (doublet), −10 ppm, −11 ppm, −12 ppm, and −19 ppm (triplet), e.g., 1.7 ppm, −7.3 ppm, −7.5 ppm (doublet), −7.6 ppm (doublet), −9.9 ppm, −10.4 ppm, −10.8 ppm, −11.6 ppm, −19.1 ppm (triplet), −19.2 ppm (triplet), and −19.3 ppm (triplet), e.g., 1.73 ppm, −7.27 ppm, −7.52 ppm (doublet), −7.62 ppm (doublet), −9.89 ppm, −10.37 ppm, −10.83 ppm, −11.62 ppm, −19.09 ppm (triplet), −19.19 ppm (triplet), and −19.29 ppm (triplet), wherein the NMR spectrum is obtained on an aqueous solution with 5 weight % D$_2$O added and is externally referenced to 85% H$_3$PO$_4$ set to 0 ppm.

1.35 Any of the foregoing complexes, wherein the complex exhibits a $^{31}$P NMR spectrum comprising the following peaks: 2 ppm, −7 ppm, −8 ppm (doublet), −10 ppm, −11 ppm, −12 ppm, and −19 ppm (triplet), e.g., 1.7 ppm, −7.3 ppm, −7.5 ppm (doublet), −7.6 ppm (doublet), −9.9 ppm, −10.4 ppm, −10.8 ppm, −11.6 ppm, −19.1 ppm (triplet), −19.2 ppm (triplet), and −19.3 ppm (triplet), e.g., 1.73 ppm, −7.27 ppm, −7.52 ppm (doublet), −7.62 ppm (doublet), −9.89 ppm, −10.37 ppm, −10.83 ppm, −11.62 ppm, −19.09 ppm (triplet), −19.19 ppm (triplet), and −19.29 ppm (triplet), wherein the NMR spectrum is obtained on an aqueous solution with 5 weight % D$_2$O added and is externally referenced to 85% H$_3$PO$_4$ set to 0 ppm.

1.36 Any of the foregoing complexes, wherein the complex exhibits a $^{31}$P NMR spectrum comprising one or more peaks selected from the group consisting of: −8 ppm (doublet) and −18 ppm (triplet), e.g., −8.3 ppm (doublet), −8.4 ppm (doublet), −17.7 ppm (triplet), −17.8 ppm (triplet), and −17.9 ppm (triplet), e.g., −8.27 ppm (doublet), −8.37 ppm (doublet), −17.69 ppm (triplet), −17.79 ppm (triplet), and −17.89 ppm (triplet), wherein the NMR spectrum is obtained on an aqueous solution with 5 weight % D$_2$O added and is externally referenced to 85% H$_3$PO$_4$ set to 0 ppm.

1.37 Any of the foregoing complexes, wherein the complex exhibits a $^{31}$P NMR spectrum comprising the following peaks: −8 ppm (doublet) and −18 ppm (triplet), e.g., −8.3 ppm (doublet), −8.4 ppm (doublet), −17.7 ppm (triplet), −17.8 ppm (triplet), and −17.9 ppm (triplet), e.g., −8.27 ppm (doublet), −8.37 ppm (doublet), −17.69 ppm (triplet), −17.79 ppm (triplet), and −17.89 ppm (triplet), wherein the NMR spectrum is obtained on an aqueous solution with 5 weight % D$_2$O added and is externally referenced to 85% H$_3$PO$_4$ set to 0 ppm.

1.38 Any of the foregoing complexes, wherein the complex exhibits a $^{31}$P NMR spectrum comprising one or more peaks selected from the group consisting of: −8 ppm (doublet), −9 ppm, and −18 ppm (triplet), e.g., −8.3 ppm (doublet), −8.4 ppm (doublet), −9.1 ppm, −17.7 ppm (triplet), −17.8 ppm (triplet), and −17.9 ppm (triplet), e.g., −8.27 ppm (doublet), −8.37 ppm (doublet), −9.07 ppm, −17.69 ppm (triplet), −17.79 ppm (triplet), and −17.89 ppm (triplet), wherein the NMR spectrum is obtained on an aqueous solution with 5 weight % D$_2$O added and is externally referenced to 85% H$_3$PO$_4$ set to 0 ppm.

1.39 Any of the foregoing complexes, wherein the complex exhibits a $^{31}$P NMR spectrum comprising the following peaks: −8 ppm (doublet), −9 ppm, and −18 ppm (triplet), e.g., −8.3 ppm (doublet), −8.4 ppm (doublet), −9.1 ppm, −17.7 ppm (triplet), −17.8 ppm (triplet), and −17.9 ppm (triplet), e.g., −8.27 ppm (doublet), −8.37 ppm (doublet), −9.07 ppm, −17.69 ppm (triplet), −17.79 ppm (triplet), and −17.89 ppm (triplet), wherein the NMR spectrum is obtained on an aqueous solution with 5 weight % D$_2$O added and is externally referenced to 85% H$_3$PO$_4$ set to 0 ppm.

Figure 5:
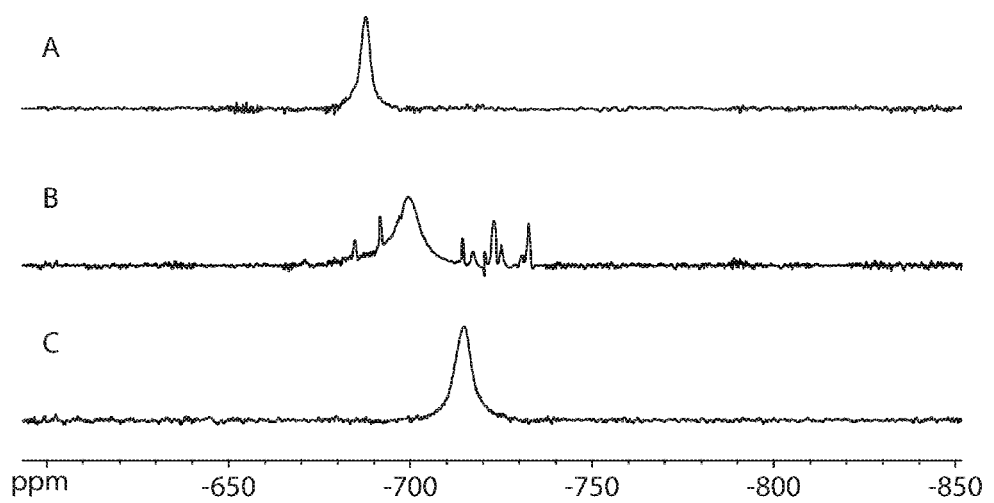
FIG. 5 depicts $^{119}Sn$ NMR spectra of solutions with P:Sn molar ratios of 10 (A), 5 (B), and 2 (C).

1.40 Any of the foregoing complexes, wherein the complex exhibits a $^{119}$Sn NMR spectrum as shown in any of the NMR spectra of FIG. 5, A, 5, B, or 5, C, wherein the NMR spectrum is obtained on an aqueous solution with 5 weight % $D_2O$ added and is externally referenced to saturated $SnF_2$ in $D_2O$ at −796 ppm.

1.41 Any of the foregoing complexes, wherein the complex exhibits a $^{119}Sn$ NMR spectrum comprising the following peak: −688 ppm, e.g., −687.9 ppm, e.g., −687.87 ppm, wherein the NMR spectrum is obtained on an aqueous solution with 5 weight % $D_2O$ added and is externally referenced to saturated $SnF_2$ in $D_2O$ at −796 ppm.

1.42 Any of the foregoing complexes, wherein the complex exhibits a $^{119}Sn$ NMR spectrum comprising the following peak: −700 ppm, e.g., −699.5 ppm, e.g., −699.51 ppm, wherein the NMR is obtained on an aqueous solution with 5 weight % $D_2O$ added and is externally referenced to saturated $SnF_2$ in $D_2O$ at −796 ppm.

1.43 Any of the foregoing complexes, wherein the complex exhibits a $^{119}Sn$ NMR spectrum comprising one or more peaks selected from the group consisting of: −685 ppm, −692 ppm, −700 ppm, −714 ppm, −717 ppm, −723 ppm, −725 ppm, and −733 ppm, e.g., −684.6 ppm, −691.7 ppm, −699.5 ppm, −714.3 ppm, −717.3 ppm, −723.0 ppm, −725.3 ppm, and −732.6 ppm, e.g., −684.61 ppm, −691.73 ppm, −699.51 ppm, −714.30 ppm, −717.32 ppm, −723.01 ppm, −725.28 ppm, and −732.59 ppm, wherein the NMR spectrum is obtained on an aqueous solution with 5 weight % $D_2O$ added and is externally referenced to saturated $SnF_2$ in $D_2O$ at −796 ppm.

1.44 Any of the foregoing complexes, wherein the complex exhibits a $^{119}Sn$ NMR spectrum comprising the following peaks: −685 ppm, −692 ppm, −700 ppm, −714 ppm, −717 ppm, −723 ppm, −725 ppm, and −733 ppm, e.g., −684.6 ppm, −691.7 ppm, −699.5 ppm, −714.3 ppm, −717.3 ppm, −723.0 ppm, −725.3 ppm, and −732.6 ppm, e.g., −684.61 ppm, −691.73 ppm, −699.51 ppm, −714.30 ppm, −717.32 ppm, −723.01 ppm, −725.28 ppm, and −732.59 ppm, wherein the NMR spectrum is obtained on an aqueous solution with 5 weight % $D_2O$ added and is externally referenced to saturated $SnF_2$ in $D_2O$ at −796 ppm.

1.45 Any of the foregoing complexes, wherein the complex exhibits a $^{119}Sn$ NMR spectrum comprising the following peak: −715 ppm, e.g., −715.0 ppm, e.g., −714.97 ppm, wherein the NMR spectrum is obtained on an aqueous solution with 5 weight % $D_2O$ added and is externally referenced to saturated $SnF_2$ in $D_2O$ at −796 ppm.

1.46 Any of the foregoing complexes, wherein the complex is formed from a mixture comprising tin (II) fluoride or tin (II) chloride and the tripolyphosphate salt, e.g., alkali tripolyphosphate salt, in a molar ratio of 1P:1Sn to less than 15P:1Sn, e.g., greater than 1P:1Sn to less than 15P:1Sn, e.g., 2P:1Sn to less than 15P:1Sn, e.g., 2P:1Sn to 10P:1Sn, e.g., 3P:1Sn to 10P:1Sn, e.g., greater than 2P:1Sn to less than 10P:1Sn, e.g., 2P:1Sn to 5P:1Sn, e.g., greater than 2P:1Sn to 5P:1Sn, e.g., 3P:1Sn to 5P:1Sn, e.g., 2P:1Sn, e.g., 3P:1Sn, e.g., 5P:1Sn. For instance, wherein the complex is formed from a mixture comprising tin (II) fluoride and the tripolyphosphate salt, e.g., alkali tripolyphosphate salt, in a molar ratio of 1P:1Sn to less than 15P:1Sn, e.g., greater than 1P:1Sn to less than 15P:1Sn, e.g., 2P:1Sn to less than 15P:1Sn, e.g., 2P:1Sn to 10P:1Sn, e.g., 2P:1Sn to 5P:1Sn, e.g., 2P:1Sn, e.g., 5P:1Sn. For instance, wherein the complex is formed from a mixture comprising tin (II) chloride and the tripolyphosphate salt, e.g., alkali tripolyphosphate salt, in a molar ratio of 2P:1Sn to 10P:1Sn, e.g., 3P:1Sn to 10P:1Sn, e.g., greater than 2P:1Sn to less than 10P:1Sn, e.g., 2P:1Sn to 5P:1Sn, e.g., greater than 2P:1Sn to 5P:1Sn, e.g., 3P:1Sn to 5P:1Sn, e.g., 3P:1Sn, e.g., 5P:1Sn.

1.47 Any of the foregoing complexes, wherein the complex is formed from a mixture comprising tin (II) fluoride or tin (II) chloride and the tripolyphosphate salt, e.g., alkali tripolyphosphate salt, in a molar ratio of 2P:1Sn to 5P:1Sn, e.g., greater than 2P:1Sn to 5P:1Sn, e.g., 3P:1Sn to 5P:1Sn, e.g., 2P:1Sn, e.g., 3P:1Sn, e.g., 5P:1Sn. For instance, wherein the complex is formed from a mixture comprising tin (II) fluoride and the tripolyphosphate salt, e.g., alkali tripolyphosphate salt, in a molar ratio of 2P:1Sn to 5P:1Sn, e.g., 2P:1Sn, e.g., 5P:1Sn. For instance, wherein the complex is formed from a mixture comprising tin (II) chloride and the tripolyphosphate salt, e.g., alkali tripolyphosphate salt, in a molar ratio of greater than 2P:1Sn to 5P:1Sn, e.g., 3P:1Sn to 5P:1Sn, e.g., 3P:1Sn, e.g., 5P:1Sn.

1.48 Any of the foregoing complexes, wherein the complex is formed from a mixture comprising tin (II) fluoride or tin (II) chloride and sodium tripolyphosphate in a molar ratio of 1P:1Sn to less than 15P:1Sn, e.g., greater than 1P:1Sn to less than 15P:1Sn, e.g., 2P:1Sn to less than 15P:1Sn, e.g., 2P:1Sn to 10P:1Sn, e.g., 3P:1Sn to 10P:1Sn, e.g., greater than 2P:1Sn to less than 10P:1Sn, e.g., 2P:1Sn to 5P:1Sn, e.g., greater than 2P:1Sn to 5P:1Sn, e.g., 3P:1Sn to 5P:1Sn, e.g., 2P:1Sn, e.g., 3P:1Sn, e.g., 5P:1Sn. For instance, wherein the complex is formed from a mixture comprising tin (II) fluoride and sodium tripolyphosphate in a molar ratio of 1P:1Sn to less than 15P:1Sn, e.g., greater than 1P:1Sn to less than 15P:1Sn, e.g., 2P:1Sn to less than 15P:1Sn, e.g., 2P:1Sn to 10P:1Sn, e.g., 2P:1Sn to 5P:1Sn, e.g., 2P:1Sn, e.g., 5P:1Sn. For instance, wherein the complex is formed from a mixture comprising tin (II) chloride and sodium tripolyphosphate in a molar ratio of 2P:1Sn to 10P:1Sn, e.g., 3P:1Sn to 10P:1Sn, e.g., greater than 2P:1Sn to less than 10P:1Sn, e.g., 2P:1Sn to 5P:1Sn, e.g., greater than 2P:1Sn to 5P:1Sn, e.g., 3P:1Sn to 5P:1Sn, e.g., 3P:1Sn, e.g., 5P:1Sn.

1.49 Complex 1.48, wherein the complex is formed from a mixture comprising tin (II) fluoride and sodium tripolyphosphate in a molar ratio of 2P:1Sn to 5P:1Sn, e.g., 2P:1Sn, e.g., 5P:1Sn.

1.50 Complex 1.48, wherein the complex is formed from a mixture comprising tin (II) chloride and sodium tripolyphosphate in a molar ratio of 2P:1Sn to less than 10P:1Sn, e.g., greater than 2P:1Sn to 5P:1Sn, e.g., 3P:1Sn to 5P:1Sn, e.g., 3P:1Sn, e.g., 5P:1Sn.

1.51 Any of the foregoing complexes, wherein the complex is formed from a mixture comprising 1-10 weight % tin (II) fluoride or tin (II) chloride by weight of the mixture, e.g., 1-9 weight % tin (II) fluoride or tin (II) chloride by weight of the mixture, e.g., 3 weight % tin (II) fluoride or tin (II) chloride by weight of the mixture, e.g., 2 weight % tin (II) fluoride or tin (II) chloride by weight of the mixture, and 1-20 weight % tripolyphosphate salt, e.g., alkali tripolyphosphate salt, by weight of the mixture, e.g., 1-15 weight % tripolyphosphate salt by weight of the mixture, e.g., more than 3 weight % tripolyphosphate salt to less than 16 weight % tripolyphosphate salt by weight of the mixture, e.g., 4-15 weight % tripolyphosphate salt by weight of the mixture, e.g., 1-10 weight % tripolyphosphate salt by weight of the mixture, e.g., 4-10 weight % tripolyphosphate salt by weight of the mixture, e.g., 3-4 weight % tripolyphosphate salt by weight of the mixture, e.g., 7-8 weight % tripolyphosphate salt by weight of the mixture. For instance, wherein the complex is formed from a mixture comprising 1-10 weight % tin (II) fluoride by weight of the mixture, e.g., 1-9 weight % tin (II) fluoride by weight of the mixture, e.g., 2 weight % tin (II) fluoride by weight of the mixture, and 1-10 weight % tripolyphosphate salt, e.g., alkali tripolyphosphate salt, by weight of the mixture, e.g., 3-4 weight % tripolyphosphate salt by weight of the mixture, e.g., 7-8 weight % tripolyphosphate salt by weight of the mixture. For instance, wherein the complex is formed from a mixture comprising 1-10 weight % tin (II) chloride by weight of the mixture, e.g., 1-9 weight % tin (II) chloride by weight of the mixture, e.g., 3 weight % tin (II) chloride by weight of the mixture, and 1-20 weight % tripolyphosphate salt, e.g., alkali tripolyphosphate salt, by weight of the mixture, e.g., 1-15 weight % tripolyphosphate salt by weight of the mixture, e.g., more than 3 weight % tripolyphosphate to less than 16 weight % tripolyphosphate salt by weight of the mixture, e.g., 4-15 weight % tripolyphosphate salt by weight of the mixture, e.g., 1-10 weight % tripolyphosphate salt by weight of the mixture, e.g., 4-10 weight % tripolyphosphate salt by weight of the mixture.

1.52 Any of the foregoing complexes, wherein the complex is formed from a mixture comprising 1-10 weight % tin (II) fluoride or tin (II) chloride by weight of the mixture, e.g., 1-9 weight % tin (II) fluoride or tin (II) chloride by weight of the mixture, e.g., 3 weight % tin (II) fluoride or tin (II) chloride by weight of the mixture, e.g., 2 weight % tin (II) fluoride or tin (II) chloride by weight of the mixture, and 1-20 weight % sodium tripolyphosphate by weight of the mixture, e.g., 1-15 weight % sodium tripolyphosphate by weight of the mixture, e.g., more than 3 weight % sodium tripolyphosphate to less than 16 weight % sodium tripolyphosphate by weight of the mixture, e.g., 4-15 weight % sodium tripolyphosphate by weight of the mixture, e.g., 1-10 weight % sodium tripolyphosphate by weight of the mixture, e.g., 4-10 weight % sodium tripolyphosphate by weight of the mixture, e.g., 3-4 weight % sodium tripolyphosphate by weight of the mixture, e.g., 7-8 weight % sodium tripolyphosphate by weight of the mixture.

1.53 Any of the foregoing complexes, wherein the complex is isolated.

1.54 Any of the foregoing complexes, wherein the complex is lyophilized.

1.55 Any of the foregoing complexes, wherein the complex is isolated with an anti-solvent, e.g., an organic solvent, e.g., ethanol.

1.56 Any of the foregoing complexes for use in an oral care composition, e.g., mouthwash, oral gel, or dentifrice.

1.57 Any of the foregoing complexes for use to reduce or inhibit dentinal hypersensitivity, dental caries, gingivitis, or plaque.

Further provided is a method (Method 1a) to reduce or inhibit one or more of dentinal hypersensitivity, dental caries, gingivitis, and plaque in a person in need thereof comprising administering an effective amount of any of Complex 1 et seq. to the oral cavity of the person.

Further provided is a method (Method 1b) of occluding dentin tubules in a person in need thereof comprising administering an effective amount of any of Complex 1 et seq. to the oral cavity of the person.

Further provided is a method (Method 2) of making an aqueous soluble tin phosphate complex, e.g., any of Complex 1 et seq., comprising combining tin (II) fluoride or tin (II) chloride and a tripolyphosphate salt, e.g., an alkali tripolyphosphate salt, e.g., potassium tripolyphosphate or sodium tripolyphosphate, e.g., 2.1 Method 2 comprising combining tin (II) fluoride and the tripolyphosphate salt, e.g., alkali tripolyphosphate salt, e.g., sodium tripolyphosphate, in an aqueous solution.

2.2 Method 2 comprising combining tin (II) chloride and the tripolyphosphate salt, e.g., alkali tripolyphosphate salt, e.g., sodium tripolyphosphate, in an aqueous solution.

2.3 Method 2.1, wherein the aqueous solution has a pH from 4-9, e.g., from 5-8, e.g., from 5-7, e.g., from 5-6, e.g., from 6-8, e.g., from 6-7, e.g., from 7-8.

2.4 Method 2.2, wherein the aqueous solution has a pH from 4-9, e.g., from 4-8, e.g., from 4-7, e.g., from 5-8, e.g., from 6-8, e.g., from 5-7, e.g., from 4-6, e.g., from 4-5, e.g., from 5-6, e.g., from 6-7, e.g., from 7-8.

2.5 Any of the foregoing methods comprising combining tin (II) fluoride or tin (II) chloride and the tripolyphosphate salt, e.g., alkali tripolyphosphate salt, in a molar ratio of 1P:1Sn to less than 15P:1Sn, e.g., greater than 1P:1Sn to less than 15P:1Sn, e.g., 2P:1Sn to less than 15P:1Sn, e.g., 2P:1Sn to 10P:1Sn, e.g., 3P:1Sn to 10P:1Sn, e.g., greater than 2P:1Sn to less than 10P:1Sn, e.g., 2P:1Sn to 5P:1Sn, e.g., greater than 2P:1Sn to 5P:1Sn, e.g., 3P:1Sn to 5P:1Sn, e.g., 2P:1Sn, e.g., 3P:1Sn, e.g., 5P:1Sn. For instance, comprising combining tin (II) fluoride and the tripolyphosphate salt, e.g., alkali tripolyphosphate salt, in a molar ratio of 1P:1Sn to less than 15P:1Sn, e.g., greater than 1P:1Sn to less than 15P:1Sn, e.g., 2P:1Sn to less than 15P:1Sn, e.g., 2P:1Sn to 10P:1Sn, e.g., 2P:1Sn to 5P:1Sn, e.g., 2P:1Sn, e.g., 5P:1Sn. For instance, comprising combining tin (II) chloride and the tripolyphosphate salt, e.g., alkali tripolyphosphate salt, in a molar ratio of 2P:1Sn to 10P:1Sn, e.g., 3P:1Sn to 10P:1Sn, e.g., greater than 2P:1Sn to less than 10P:1Sn, e.g., 2P:1Sn to 5P:1Sn, e.g., greater than 2P:1Sn to 5P:1Sn, e.g., 3P:1Sn to 5P:1Sn, e.g., 3P:1Sn, e.g., 5P:1Sn.

2.6 Any of the foregoing methods, wherein the tripolyphosphate salt is sodium tripolyphosphate.

2.7 Any of the foregoing methods comprising combining tin (II) fluoride or tin (II) chloride and sodium tripolyphosphate in a molar ratio of 1P:1Sn to less than 15P:1Sn, e.g., greater than 1P:1Sn to less than 15P:1Sn, e.g., 2P:1Sn to less than 15P:1Sn, e.g., 2P:1Sn to 10P:1Sn, e.g., 3P:1Sn to 10P:1Sn, e.g., greater than 2P:1Sn to less than 10P:1Sn, e.g., 2P:1Sn to 5P:1Sn, e.g., greater than 2P:1Sn to 5P:1Sn, e.g., 3P:1Sn to 5P:1Sn, e.g., 2P:1Sn, e.g., 3P:1Sn, e.g., 5P:1Sn. For instance, comprising combining tin (II) fluoride and sodium tripolyphosphate in a molar ratio of 1P:1Sn to less than 15P:1Sn, e.g., greater than 1P:1Sn to less than 15P:1Sn, e.g., 2P:1Sn to less than 15P:1Sn, e.g., 2P:1Sn to 10P:1Sn, e.g., 2P:1Sn to 5P:1Sn, e.g., 2P:1Sn, e.g., 5P:1Sn. For instance, comprising combining tin (II) chloride and sodium tripolyphosphate in a molar ratio of 2P:1Sn to 10P 1Sn, e.g., 3P:1Sn to 10P:1Sn, e.g., greater than 2P:1Sn to less than 10P:1Sn, e.g., 2P 1Sn to 5P:1Sn, e.g., greater than 2P:1Sn to 5P:1Sn, e.g., 3P:1Sn to 5P:1Sn, e.g., 3P 1Sn, e.g., 5P:1Sn.

2.8 Method 2.7 comprising combining tin (II) fluoride and sodium tripolyphosphate in a molar ratio of 2P:1Sn to 5P:1Sn, e.g., 2P:1Sn, e.g., 5P:1Sn.

2.9 Method 2.7 comprising combining tin (II) chloride and sodium tripolyphosphate in a molar ratio of greater than 2P:1Sn to less than 10P:1Sn, e.g., greater than 2P:1Sn to 5P: 1Sn, e.g., 3P:1Sn to 5P:1Sn, e.g., 3P:1Sn, e.g., 5P:1Sn.

2.10 Any of the foregoing methods comprising combining 1-10 weight % tin (II) fluoride or tin (II) chloride by weight of the combination, e.g., 1-9 weight % tin (II) fluoride or tin (II) chloride by weight of the combination, e.g., 3 weight % tin (II) fluoride or tin (II) chloride by weight of the combination, e.g., 2 weight % tin (II) fluoride or tin (II) chloride by weight of the combination, and 1-20 weight % tripolyphosphate salt, e.g., alkali tripolyphosphate salt by weight of the combination, e.g., 1-15 weight % tripolyphosphate salt by weight of the combination, e.g., more than 3 weight % tripolyphosphate salt to less than 16 weight % tripolyphosphate salt by weight of the combination, e.g., 4-15 weight % tripolyphosphate salt by weight of the combination, e.g., 1-10 weight % tripolyphosphate salt by weight of the combination, e.g., 4-10 weight % tripolyphosphate salt by weight of the combination, e.g., 3-4 weight % tripolyphosphate salt by weight of the combination, e.g., 7-8 weight % tripolyphosphate salt by weight of the combination. For instance, comprising combining 1-10 weight % tin (II) fluoride by weight of the combination, e.g., 1-9 weight % tin (II) fluoride by weight of the combination, e.g., 2 weight % tin (II) fluoride by weight of the combination, and 1-10 weight % tripolyphosphate salt, e.g., alkali tripolyphosphate salt, by weight of the combination, e.g., 3-4 weight % tripolyphosphate salt by weight of the combination, e.g., 7-8 weight % tripolyphosphate salt by weight of the combination. For instance, comprising combining 1-10 weight % tin (II) chloride by weight of the combination, e.g., 1-9 weight % tin (II) chloride by weight of the combination, e.g., 3 weight % tin (II) chloride by weight of the combination, and 1-20 weight % tripolyphosphate salt, e.g., alkali tripolyphosphate salt, by weight of the combination, e.g., 1-15 weight % tripolyphosphate salt by weight of the combination, e.g., more than 3 weight % tripolyphosphate salt to less than 16 weight % tripolyphosphate salt by weight of the combination, e.g., 4-15 weight % tripolyphosphate salt by weight of the combination, e.g., 1-10 weight % tripolyphosphate salt by weight of the combination, e.g., 4-10 weight % tripolyphosphate salt by weight of the combination.

2.11 Any of the foregoing methods comprising combining 1-10 weight % tin (II) fluoride or tin (II) chloride by weight of the combination, e.g., 1-9 weight % tin (II) fluoride or tin (II) chloride by weight of the combination, e.g., 3 weight % tin (II) fluoride or tin (II) chloride by weight of the combination, e.g., 2 weight % tin (II) fluoride or tin (II) chloride by weight of the combination, and 1-20 weight % sodium tripolyphosphate by weight of the combination, e.g., more than 3 weight % sodium tripolyphosphate to less than 16 weight % sodium tripolyphosphate by weight of the combination, e.g., 4-15 weight % sodium tripolyphosphate by weight of the combination, e.g., 1-10 weight % sodium tripolyphosphate by weight of the combination, e.g., 4-10 weight % sodium tripolyphosphate by weight of the combination, e.g., 3-4 weight % sodium tripolyphosphate by weight of the combination, e.g., 7-8 weight % sodium tripolyphosphate by weight of the combination. For instance, comprising combining 1-10 weight % tin (II) fluoride by weight of the combination, e.g., 1-9 weight % tin (II) fluoride by weight of the combination, e.g., 2 weight % tin (II) fluoride by weight of the combination, and 1-10 weight % sodium tripolyphosphate by weight of the combination, e.g., 3-4 weight % sodium tripolyphosphate by weight of the combination, e.g., 7-8 weight % sodium tripolyphosphate by weight of the combination. For instance, comprising combining 1-10 weight % tin (II) chloride by weight of the combination, e.g., 1-9 weight % tin (II) chloride by weight of the combination, e.g., 3 weight % tin (II) chloride by weight of the combination, and 1-20 weight % sodium tripolyphosphate by weight of the combination, e.g., 1-15 weight % sodium tripolyphosphate by weight of the combination, e.g., more than 3 weight % sodium tripolyphosphate to less than 16 weight % sodium tripolyphosphate by weight of the combination, e.g., 4-15 weight % sodium tripolyphosphate by weight of the combination, e.g., 1-10 weight % sodium tripolyphosphate by weight of the combination, e.g., 4-10 weight % sodium tripolyphosphate by weight of the combination.

2.12 Any of the foregoing methods comprising isolating the complex in solid form.

2.13 Any of the foregoing methods comprising lyophilizing the complex.

2.14 Any of the foregoing methods comprising isolating the complex with an anti-solvent, e.g., an organic solvent, e.g., ethanol.

2.15 An oral care composition, e.g., a mouthwash, oral gel, or dentifrice, e.g., a mouthwash, comprising an aqueous soluble tin phosphate complex made as described in any of the foregoing methods.

Further provided is an aqueous soluble tin phosphate complex made by any of Method 2 et seq.

Further provided is an oral care composition (Composition 1) comprising an aqueous soluble tin phosphate complex formed from a mixture comprising tin (II) fluoride or tin (II) chloride and a tripolyphosphate salt, e.g., an alkali tripolyphosphate salt, e.g., potassium tripolyphosphate ($K_5P_3O_{10}$) or sodium tripolyphosphate ($Na_5P_3O_{10}$) (STPP), e.g., any of Complex 1 et seq., e.g., 1.1 Composition 1, wherein the tripolyphosphate salt is sodium tripolyphosphate ($Na_5P_3O_{10}$).

1.2 Composition 1 or 1.1, wherein the complex is formed in the composition in situ, e.g., wherein the composition has a pH from 4-9, e.g., from 5-8, e.g., from 5-7, e.g., from 5-6, e.g., from 6-8, e.g., from 6-7, e.g., from 7-8. For instance, wherein the complex is formed in situ in the composition from tin (II) fluoride and the tripolyphosphate salt, e.g., alkali tripolyphosphate salt, e.g., wherein the composition has a pH from 4-9, e.g., from 5-8, e.g., from 5-7, e.g., from 5-6, e.g., from 6-8, e.g., from 6-7, e.g., from 7-8. For instance, wherein the complex is formed in situ in the composition from tin (II) chloride and the tripolyphosphate salt, e.g., alkali tripolyphosphate salt, e.g., wherein the composition has a pH from 4-8, e.g., from 4-7, e.g., from 5-8, e.g., from 5-7, e.g., from 4-6, e.g., from 4-5, e.g., from 5-6, e.g., from 6-7, e.g., from 7-8.

1.3 Any of Composition 1 or 1.1, wherein the complex is formed in situ in an aqueous solution and combined with the composition, e.g., wherein the aqueous solution has a pH from 4-9, e.g., from 5-8, e.g., from 5-7, e.g., from 5-6, e.g., from 6-8, e.g., from 6-7, e.g., from 7-8. For instance, wherein the complex is formed in situ in an aqueous solution from tin (II) fluoride and the tripolyphosphate salt, e.g., alkali tripolyphosphate salt, e.g., wherein the aqueous solution has a pH from 4-9, e.g., from 5-8, e.g., from 5-7, e.g., from 5-6, e.g., from 6-8, e.g., from 6-7, e.g., from 7-8. For instance, wherein the complex is formed in situ in an aqueous solution from tin (II) chloride and the tripolyphosphate salt, e.g., alkali tripolyphosphate salt, e.g., wherein the aqueous solution has a pH from 4-9, e.g., from 4-8, e.g., from 4-7, e.g., from 5-8, e.g., from 6-8, e.g., from 5-7, e.g., from 4-6, e.g., from 4-5, e.g., from 5-6, e.g., from 6-7, e.g., from 7-8.

1.4 Any of Composition 1, 1.1, or 1.3, wherein the complex is combined as a solid with the composition, e.g., wherein the complex is isolated from the aqueous solution in solid form and combined with the composition.

1.5 Any of Composition 1, 1.1, 1.3, or 1.4, wherein the complex is lyophilized and combined with the composition.

1.6 Any of Composition 1, 1.1, or 1.3-1.5, wherein the complex is isolated with an anti-solvent, e.g., an organic solvent, e.g., ethanol, and combined with the composition.

1.7 Any of the foregoing compositions, wherein the complex is made as described in any of Method 2 et seq.

1.8 Any of the foregoing compositions, wherein the complex is present in an amount of 2-30 weight % by weight of the composition.

1.9 Any of the foregoing compositions, wherein the complex is formed from tin (II) fluoride or tin (II) chloride and the tripolyphosphate salt, e.g., alkali tripolyphosphate salt, in a molar ratio of 1P:1Sn to less than 15P:1Sn, e.g., greater than 1P:1Sn to less than 15P:1Sn, e.g., 2P:1Sn to less than 15P:1Sn, e.g., 2P:1Sn to 10P:1Sn, e.g., 3P:1Sn to 10P:1Sn, e.g., greater than 2P:1Sn to less than 10P:1Sn, e.g., 2P:1Sn to 5P:1Sn, e.g., greater than 2P:1Sn to 5P:1Sn, e.g., 3P:1Sn to 5P:1Sn, e.g., 2P:1Sn, e.g., 3P:1Sn, e.g., 5P:1Sn. For instance, wherein the complex is formed from tin (II) fluoride and the tripolyphosphate salt, e.g., alkali tripolyphosphate salt, in a molar ratio of 1P:1Sn to less than 15P:1Sn, e.g., greater than 1P:1Sn to less than 15P:1Sn, e.g., 2P:1Sn to less than 15P:1Sn, e.g., 2P: 1Sn to 10P:1Sn, e.g., 2P:1Sn to 5P:1Sn, e.g., 2P:1Sn, e.g., 5P:1Sn. For instance, wherein the complex is formed from tin (II) chloride and the tripolyphosphate salt, e.g., alkali tripolyphosphate salt, in a molar ratio of 2P:1Sn to 10P:1Sn, e.g., 3P:1Sn to 10P:1Sn, e.g., greater than 2P:1Sn to less than 10P:1Sn, e.g., 2P:1Sn to 5P:1Sn, e.g., greater than 2P:1Sn to 5P:1Sn, e.g., 3P:1Sn to 5P:1Sn, e.g., 3P:1Sn, e.g., 5P:1Sn.

1.10 Any of the foregoing compositions, wherein the complex is formed from tin (II) fluoride or tin (II) chloride and sodium tripolyphosphate in a molar ratio of 1P:1Sn to less than 15P: 1Sn, e.g., greater than 1P:1Sn to less than 15P:1Sn, e.g., 2P:1Sn to less than 15P:1Sn, e.g., 2P:1Sn to 10P:1Sn, e.g., 3P:1Sn to 10P:1Sn, e.g., greater than 2P:1Sn to less than 10P:1Sn, e.g., 2P:1Sn to 5P:1Sn, e.g., 3P:1Sn to 5P:1Sn, e.g., 2P:1Sn, e.g., 3P:1Sn, e.g., 5P:1Sn. For instance, wherein the complex is formed from tin (II) fluoride and sodium tripolyphosphate in a molar ratio of 1P:1Sn to less than 15P:1Sn, e.g., greater than 1P: 1Sn to less than 15P:1Sn, e.g., 2P:1Sn to less than 15P:1Sn, e.g., 2P:1Sn to 10P:1Sn, e.g., 2P:1Sn to 5P:1Sn, e.g., 2P:1Sn, e.g., 5P:1Sn. For instance, wherein the complex is formed from tin (II) chloride and sodium tripolyphosphate in a molar ratio of 2P:1Sn to 10P:1Sn, e.g., 3P:1Sn to 10P:1Sn, e.g., greater than 2P:1Sn to less than 10P:1Sn, e.g., 2P:1Sn to 5P:1Sn, e.g., greater than 2P:1Sn to 5P:1Sn, e.g., 3P:1Sn to 5P:1Sn, e.g., 3P:1Sn, e.g., 5P:1Sn.

1.11 Composition 1.10, wherein the complex is formed from tin (II) fluoride and sodium tripolyphosphate in a molar ratio of 2P:1Sn to 5P:1Sn, e.g., 2P:1Sn, e.g., 5P:1Sn.

1.12 Composition 1.10, wherein the complex is formed from tin (II) chloride and sodium tripolyphosphate in a molar ratio of greater than 2P:1Sn to less than 10P:1Sn, e.g., greater than 2P:1Sn to 5P:1Sn e.g., 3P:1Sn to 5P:1Sn, e.g., 3P:1Sn, e.g., 5P:1Sn.

1.13 Any of the foregoing compositions, wherein the complex is formed from a mixture comprising 1-10 weight % tin (II) fluoride or tin (II) chloride by weight of the mixture, e.g., 1-9 weight % tin (II) fluoride or tin (II) chloride by weight of the mixture, e.g., 3 weight % tin (II) fluoride or tin (II) chloride by weight of the mixture, e.g., 2 weight % tin (II) fluoride or tin (II) chloride by weight of the mixture, and 1-20 weight % tripolyphosphate salt, e.g., alkali tripolyphosphate salt, by weight of the mixture, e.g., 1-15 weight % tripolyphosphate salt by weight of the mixture, e.g., more than 3 weight % tripolyphosphate salt to less than 16 weight % tripolyphosphate salt by weight of the mixture, e.g., 4-15 weight % tripolyphosphate salt by weight of the mixture, e.g., 1-10 weight % tripolyphosphate salt by weight of the mixture, e.g., 4-10 weight % tripolyphosphate salt by weight of the mixture, e.g., 3-4 weight % tripolyphosphate salt by weight of the mixture, e.g., 7-8 weight % tripolyphosphate salt by weight of the mixture. For instance, wherein the complex is formed from a mixture comprising 1-10 weight % tin (II) fluoride by weight of the mixture, e.g., 1-9 weight % tin (II) fluoride by weight of the mixture, e.g., 2 weight % tin (II) fluoride by weight of the mixture, and 1-10 weight % tripolyphosphate salt, e.g., alkali tripolyphosphate salt, by weight of the mixture, e.g., 3-4 weight % tripolyphosphate salt by weight of the mixture, e.g., 7-8 weight % tripolyphosphate salt by weight of the mixture. For instance, wherein the complex is formed from a mixture comprising 1-10 weight % tin (II) chloride by weight of the mixture, e.g., 1-9 weight % tin (II) chloride by weight of the mixture, e.g., 3 weight % tin (II) chloride by weight of the mixture, and 1-20 weight % tripolyphosphate salt, e.g., alkali tripolyphosphate salt, by weight of the mixture, e.g., 1-15 weight % tripolyphosphate salt by weight of the mixture, e.g., more than 3 weight % tripolyphosphate salt to less than 16 weight % tripolyphosphate salt by weight of the mixture, e.g., 4-15 weight % tripolyphosphate salt by weight of the mixture, e.g., 1-10 weight % tripolyphosphate salt by weight of the mixture, e.g., 4-10 weight % tripolyphosphate salt by weight of the mixture.

1.14 Any of the foregoing compositions, wherein the complex is formed from a mixture comprising 1-10 weight % tin (II) fluoride or tin (II) chloride by weight of the mixture, e.g., 1-9 weight % tin (II) fluoride or tin (II) chloride by weight of the mixture, e.g., 3 weight % tin (II) fluoride or tin (II) chloride by weight of the mixture, e.g., 2 weight % tin (II) fluoride or tin (II) chloride by weight of the mixture, and 1-20 weight % sodium tripolyphosphate by weight of the mixture, e.g., more than 3 weight % sodium tripolyphosphate to less than 16 weight % sodium tripolyphosphate by weight of the mixture, e.g., 4-15 weight % sodium tripolyphosphate by weight of the mixture, e.g., 1-10 weight % sodium tripolyphosphate by weight of the mixture, e.g., 4-10 weight % sodium tripolyphosphate by weight of the mixture, e.g., 3-4 weight % sodium tripolyphosphate by weight of the mixture, e.g., 7-8 weight % sodium tripolyphosphate by weight of the mixture. For instance, wherein the complex is formed from a mixture comprising 1-10 weight % tin (II) fluoride by weight of the mixture, e.g., 1-9 weight % tin (II) fluoride by weight of the mixture, e.g., 2 weight % tin (II) fluoride by weight of the mixture, and 1-10 weight % sodium tripolyphosphate by weight of the mixture, e.g., 3-4 weight % sodium tripolyphosphate by weight of the mixture, e.g., 7-8 weight % sodium tripolyphosphate by weight of the mixture. For instance, wherein the complex is formed from a mixture comprising 1-10 weight % tin (II) chloride by weight of the mixture, e.g., 1-9 weight % tin (II) chloride by weight of the mixture, e.g., 3 weight % tin (II) chloride by weight of the mixture, and 1-20 weight % sodium tripolyphosphate by weight of the mixture, e.g., 1-15 weight % sodium tripolyphosphate by weight of the mixture, e.g., more than 3 weight % sodium tripolyphosphate to less than 16 weight % sodium tripolyphosphate by weight of the mixture, e.g., 4-15 weight % tripolyphosphate salt by weight of the mixture, e.g., 1-10 weight % tripolyphosphate salt by weight of the mixture, e.g., 4-10 weight % tripolyphosphate salt by weight of the mixture.

1.15 Any of the foregoing compositions, wherein the composition comprises an aqueous solution.

1.16 Any of the foregoing compositions further comprising a fluoride ion source, e.g., a fluoride ion source selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

1.17 Composition 1.16, wherein the fluoride ion source is present in an amount of 0.01-5 weight % by weight of the composition, e.g., 0.01-2 weight % by weight of the composition, e.g., 0.01-1 weight % by weight of the composition.

1.18 Any of the foregoing compositions further comprising another alkali phosphate salt.

1.19 Composition 1.18, wherein the alkali phosphate salt is present in an amount of 1-10 weight % by weight of the composition.

1.20 Any of the foregoing compositions further comprising a humectant, e.g., a humectant selected from glycerin, sorbitol, propylene glycol, polyethylene glycol, xylitol, and combinations thereof.

1.21 Composition 1.20, wherein the humectant is present in an amount of 2-50 weight % by weight of the composition, e.g., 10-40 weight % by weight of the composition, e.g., 15-30 weight % by weight of the composition.

1.22 Any of the foregoing compositions further comprising a surfactant, e.g., selected from anionic, cationic, zwitterionic, and nonionic surfactants, and combinations thereof, e.g., selected from sodium lauryl sulfate, sodium ether lauryl sulfate, cocamidopropylbetaine, a poloxamer, and combinations thereof.

1.23 Composition 1.22, wherein the surfactant is present in an amount of 1-10 weight % by weight of the composition.

1.24 Any of the foregoing compositions further comprising a thickener, e.g., selected from a polysaccharide gums, e.g., xanthan gum and/or carrageenan, a silica thickener, a cellulosic polymer, e.g., sodium CMC, and combinations thereof.

1.25 Composition 1.24, wherein the thickener is present in an amount of 1-10 weight % by weight of the composition.

1.26 Any of the foregoing compositions further comprising an abrasive, e.g., silica abrasive.

1.27 Composition 1.26, wherein the abrasive is present in an amount of 10-30 weight % by weight of the composition.

1.28 Any of the foregoing compositions further comprising a pH agent to adjust the pH, e.g., selected from sodium bicarbonate, an alkali phosphate, sodium hydroxide, citric acid, sodium citrate, and combinations thereof.

1.29 Composition 1.28, wherein the pH agent is present in an amount of 0.1-10 weight % by weight of the composition, e.g., 1-5 weight % by weight of the composition, e.g., 1-3 weight % by weight of the composition.

1.30 Any of the foregoing compositions further comprising flavoring, fragrance, and/or coloring.

1.31 Any of the foregoing compositions further comprising 2-90 weight % water by weight of the composition, e.g., 2-50 weight % water by weight of the composition, e.g., 50-80 weight % water by weight of the composition.

1.32 Any of the foregoing compositions comprising more than 20 weight % water by weight of the composition, e.g., at least 30 weight % water by weight of the composition, e.g., at least 40 weight % water by weight of the composition, e.g., at least 50 weight % water by weight of the composition, e.g., at least 60 weight % water by weight of the composition, e.g., at least 70 weight % water by weight of the composition.

1.33 Any of the foregoing compositions, wherein the composition comprises tin (II) fluoride.

1.34 Any of Composition 1 or 1.1-1.32, wherein the composition comprises tin (II) chloride.

1.35 Composition 1.33, wherein the composition has a pH from 4-9, e.g., from 5-8, e.g., from 5-7, e.g., from 5-6, e.g., from 6-8, e.g., from 6-7, e.g., from 7-8.

1.36 Composition 1.34, wherein the composition has a pH from 4-9, e.g., from 4-8, e.g., from 4-7, e.g., from 5-8, e.g., from 6-8, e.g., from 5-7, e.g., from 4-6, e.g., from 4-5, e.g., from 5-6, e.g., from 6-7, e.g., from 7-8.

1.37 Any of the foregoing compositions, wherein the composition is a mouthwash, oral gel, or dentifrice, e.g., a mouthwash.

1.38 Any of the foregoing compositions for use to reduce or inhibit dentinal hypersensitivity, dental caries, gingivitis, or plaque.

Further provided is a method (Method 3a) to reduce or inhibit one or more of dentinal hypersensitivity, dental caries, gingivitis, and plaque in a person in need thereof comprising administering an effective amount of an oral care composition comprising an aqueous soluble tin phosphate complex formed from a mixture comprising tin (II) fluoride or tin (II) chloride and a tripolyphosphate salt, e.g., an alkali tripolyphosphate salt, e.g., potassium tripolyphosphate ($K_5P_3O_{10}$) or sodium tripolyphosphate ($Na_5P_3O_{10}$), e.g., any of Composition 1 et seq., to the oral cavity of the person.

Further provided is a method (Method 3b) of occluding dentin tubules in a person in need thereof comprising administering an effective amount of an oral care composition comprising an aqueous soluble tin phosphate complex formed from a mixture comprising tin (II) fluoride or tin (II) chloride and a tripolyphosphate salt, e.g., an alkali tripolyphosphate salt, e.g., potassium tripolyphosphate ($K_5P_3O_{10}$) or sodium tripolyphosphate ($Na_5P_3O_{10}$), e.g., any of Composition 1 et seq., to the oral cavity of the person.

Further provided is Method 3a and/or 3b as follows:

3.1 Method 3a or 3b, wherein the complex is any of Complex 1 et seq.

3.2 Any of Method 3a, 3b, or 3.1, wherein the complex is formed in situ in the composition, e.g., wherein the composition has a pH from 4-9, e.g., from 5-8, e.g., from 5-7, e.g., from 5-6, e.g., from 6-8, e.g., from 6-7, e.g., from 7-8. For instance, wherein the complex is formed in situ in the composition from tin (II) fluoride and the tripolyphosphate salt, e.g., alkali tripolyphosphate salt, e.g., wherein the composition has a pH from 4-9, e.g., from 5-8, e.g., from 5-7, e.g., from 5-6, e.g., from 6-8, e.g., from 6-7, e.g., from 7-8. For instance, wherein the complex is formed in situ in the composition from tin (II) chloride and the tripolyphosphate salt, e.g., alkali tripolyphosphate salt, e.g., wherein the composition has a pH from 4-9, e.g., from 4-8, e.g., from 4-7, e.g., from 5-8, e.g., from 6-8, e.g., from 5-7, e.g., from 4-6, e.g., from 4-5, e.g., from 5-6, e.g., from 6-7, e.g., from 7-8.

3.3 Any of Method 3a, 3b, or 3.1, wherein the complex is formed in situ in an aqueous solution and combined with the composition, e.g., wherein the aqueous solution has a pH from 4-9, e.g., from 5-8, e.g., from 5-7, e.g., from 5-6, e.g., from 6-8, e.g., from 6-7, e.g., from 7-8. For instance, wherein the complex is formed in situ in an aqueous solution from tin (II) fluoride and the tripolyphosphate salt, e.g., alkali tripolyphosphate salt, e.g., wherein the aqueous solution has a pH from 4-9, e.g., from 5-8, e.g., from 5-7, e.g., from 5-6, e.g., from 6-8, e.g., from 6-7, e.g., from 7-8. For instance, wherein the complex is formed in situ in an aqueous solution from tin (II) chloride and the tripolyphosphate salt, e.g., alkali tripolyphosphate salt, e.g., wherein the aqueous solution has a pH from 4-9, e.g., from 4-8, e.g., from 4-7, e.g., from 5-8, e.g., from 6-8, e.g., from 5-7, e.g., from 4-6, e.g., from 4-5, e.g., from 5-6, e.g., from 6-7, e.g., from 7-8.

3.4 Any of Method 3a, 3b, 3.1, or 3.3, wherein the complex is combined as a solid with the composition, e.g., wherein the complex is isolated from the aqueous solution in solid form and combined with the composition, e.g., mouthwash.

3.5 Any of Method 3a, 3b, 3.1, 3.3, or 3.4, wherein the complex is lyophilized and combined with the composition.

3.6 Any of Method 3a, 3b, 3.1, or 3.3-3.5, wherein the complex is isolated with an anti-solvent, e.g., an organic solvent, e.g., ethanol, and combined with the composition.

3.7 Any of the foregoing methods, wherein the complex is made as described in any of Method 2 et seq.

3.8 Any of the foregoing methods, wherein the complex is present in an amount of 2-30 weight % by weight of the composition.

3.9 Any of the foregoing methods, wherein the tripolyphosphate salt is sodium tripolyphosphate ($Na_5P_3O_{10}$).

3.10 Any of the foregoing methods, wherein the complex is formed from tin (II) fluoride or tin (II) chloride and the tripolyphosphate salt, e.g., alkali tripolyphosphate salt, in a molar ratio of 1P:1Sn to less than 15P:1Sn, e.g., greater than 1P:1Sn to less than 15P:1Sn, e.g., 2P:1Sn to less than 15P:1Sn, e.g., 2P:1Sn to 10P:1Sn, e.g., 3P:1Sn to 10P:1Sn, e.g., greater than 2P:1Sn to less than 10P:1Sn, e.g., 2P:1Sn to 5P:1Sn, e.g., greater than 2P: 1Sn to 5P:1Sn, e.g., 3P:1Sn to 5P:1Sn, e.g., 2P:1Sn, e.g., 3P:1Sn, e.g., 5P:1Sn. For instance, wherein the complex is formed from tin (II) fluoride and the tripolyphosphate salt, e.g., alkali tripolyphosphate salt, in a molar ratio of 1P:1Sn to less than 15P:1Sn, e.g., greater than 1P:1Sn to less than 15P:1Sn, e.g., 2P:1Sn to less than 15P:1Sn, e.g., 2P: 1Sn to 10P:1Sn, e.g., 2P:1Sn to 5P:1Sn, e.g., 2P:1Sn, e.g., 5P:1Sn. For instance, wherein the complex is formed from tin (II) chloride and the tripolyphosphate salt, e.g., alkali tripolyphosphate salt, in a molar ratio of 2P:1Sn to 10P:1Sn, e.g., 3P:1Sn to 10P: 1Sn, e.g., greater than 2P:1Sn to less than 10P:1Sn, e.g., 2P:1Sn to 5P:1Sn, e.g., greater than 2P:1Sn to 5P:1Sn, e.g., 3P:1Sn to 5P:1Sn, e.g., 3P:1Sn, e.g., 5P:1Sn.

3.11 Any of the foregoing methods, wherein the complex is formed from tin (II) fluoride or tin (II) chloride and sodium tripolyphosphate in a molar ratio of 1P:1Sn to less than 15P:1Sn, e.g., greater than 1P:1Sn to less than 15P:1Sn, e.g., 2P:1Sn to less than 15P:1Sn, e.g., 2P:1Sn to 10P:1Sn, e.g., 3P:1Sn to 10P:1Sn, e.g., greater than 2P:1Sn to less than 10P: 1Sn, e.g., 2P:1Sn to 5P:1Sn, e.g., greater than 2P:1Sn to 5P:1Sn, e.g., 3P:1Sn to 5P: 1Sn, e.g., 2P:1Sn, e.g., 3P:1Sn, e.g., 5P:1Sn. For instance, wherein the complex is formed from tin (II) fluoride and sodium tripolyphosphate in a molar ratio of 1P:1Sn to less than 15P:1Sn, e.g., greater than 1P:1Sn to less than 15P:1Sn, e.g., 2P:1Sn to less than 15P:1Sn, e.g., 2P:1Sn to 10P:1Sn, e.g., 2P:1Sn to 5P:1Sn, e.g., 2P:1Sn, e.g., 5P: 1Sn. For instance, wherein the complex is formed from tin (II) chloride and sodium tripolyphosphate in a molar ratio of 2P:1Sn to 10P:1Sn, e.g., 3P:1Sn to 10P:1Sn, e.g., greater than 2P:1Sn to less than 10P:1Sn, e.g., 2P:1Sn to 5P:1Sn, e.g., greater than 2P: 1Sn to 5P:1Sn, e.g., 3P:1Sn to 5P:1Sn, e.g., 3P:1Sn, e.g., 5P:1Sn.

3.12 Method 3.11, wherein the complex is formed from tin (II) fluoride and sodium tripolyphosphate in a molar ratio of 2P:1Sn to 5P:1Sn, e.g., 2P:1Sn, e.g., 5P:1Sn.

3.13 Method 3.11, wherein the complex is formed from tin (II) chloride and sodium tripolyphosphate in a molar ratio of greater than 2P:1Sn to 5P:1Sn, e.g., 3P:1Sn to 5P: 1Sn, e.g., 3P:1Sn, e.g., 5P:1Sn.

3.14 Any of the foregoing methods, wherein the complex is formed from a mixture comprising 1-10 weight % tin (II) fluoride or tin (II) chloride by weight of the mixture, e.g., 1-9 weight % tin (II) fluoride or tin (II) chloride by weight of the mixture, e.g., 3 weight % tin (II) fluoride or tin (II) chloride by weight of the mixture, e.g., 2 weight % tin (II) fluoride or tin (II) chloride by weight of the mixture, and 1-20 weight % tripolyphosphate salt, e.g., alkali tripolyphosphate salt, by weight of the mixture, e.g., 1-15 weight % tripolyphosphate salt by weight of the mixture, e.g., more than 3 weight % tripolyphosphate salt to less than 16 weight % tripolyphosphate salt by weight of the mixture, e.g., 4-15 weight % tripolyphosphate salt by weight of the mixture, e.g., 1-10 weight % tripolyphosphate salt by weight of the mixture, e.g., 4-10 weight % tripolyphosphate salt by weight of the mixture, e.g., 3-4 weight % tripolyphosphate salt by weight of the mixture, e.g., 7-8 weight % tripolyphosphate salt by weight of the mixture. For instance, wherein the complex is formed from a mixture comprising 1-10 weight % tin (II) fluoride by weight of the mixture, e.g., 1-9 weight % tin (II) fluoride by weight of the mixture, e.g., 2 weight % tin (II) fluoride by weight of the mixture, and 1-10 weight % tripolyphosphate salt, e.g., alkali tripolyphosphate salt, by weight of the mixture, e.g., 3-4 weight % tripolyphosphate salt by weight of the mixture, e.g., 7-8 weight % tripolyphosphate salt by weight of the mixture. For instance, wherein the complex is formed from a mixture comprising 1-10 weight % tin (II) chloride by weight of the mixture, e.g., 1-9 weight % tin (II) chloride by weight of the mixture, e.g., 3 weight % tin (II) chloride by weight of the mixture, and 1-20 weight % tripolyphosphate salt, e.g., alkali tripolyphosphate salt, by weight of the mixture, e.g., 1-15 weight % tripolyphosphate salt by weight of the mixture, e.g., more than 3 weight % tripolyphosphate salt to less than 16 weight % tripolyphosphate salt by weight of the mixture, e.g., 4-15 weight % tripolyphosphate salt by weight of the mixture, e.g., 1-10 weight % tripolyphosphate salt by weight of the mixture, e.g., 4-10 weight % tripolyphosphate salt by weight of the mixture.

3.15 Any of the foregoing methods, wherein the complex is formed from a mixture comprising 1-10 weight % tin (II) fluoride or tin (II) chloride by weight of the mixture, e.g., 1-9 weight % tin (II) fluoride or tin (II) chloride by weight of the mixture, e.g., 3 weight % tin (II) fluoride or tin (II) chloride by weight of the mixture, e.g., 2 weight % tin (II) fluoride or tin (II) chloride by weight of the mixture, and 1-20 weight % sodium tripolyphosphate by weight of the mixture, e.g., and 1-15 weight % sodium tripolyphosphate by weight of the mixture, e.g., more than 3 weight % sodium tripolyphosphate to less than 16 weight % sodium tripolyphosphate by weight of the mixture, e.g., 4-15 weight % sodium tripolyphopshate by weight of the mixture, e.g., 1-10 weight % sodium tripolyphosphate by weight of the mixture, e.g., 4-10 weight % sodium tripolyphopshate by weight of the mixture, e.g., 3-4 weight % sodium tripolyphosphate by weight of the mixture, e.g., 7-8 weight % sodium tripolyphosphate by weight of the mixture. For instance, wherein the complex is formed from a mixture comprising 1-10 weight % tin (II) fluoride by weight of the mixture, e.g., 1-9 weight % tin (II) fluoride by weight of the mixture, e.g., 2 weight % tin (II) fluoride by weight of the mixture, and 1-10 weight % sodium tripolyphosphate by weight of the mixture, e.g., 3-4 weight % sodium tripolyphosphate by weight of the mixture, e.g., 7-8 weight % sodium tripolyphosphate by weight of the mixture. For instance, wherein the complex is formed from a mixture comprising 1-10 weight % tin (II) chloride by weight of the mixture, e.g., 1-9 weight % tin (II) chloride by weight of the mixture, e.g., 3 weight % tin (II) chloride by weight of the mixture, and 1-20 weight % sodium tripolyphosphate by weight of the mixture, e.g., 1-15 weight % sodium tripolyphosphate by weight of the mixture, e.g., more than 3 weight % sodium tripolyphosphate to less than 16 weight % sodium tripolyphosphate by weight of the mixture, e.g., 4-15 weight % sodium tripolyphosphate by weight of the mixture, e.g., 1-10 weight % sodium tripolyphosphate by weight of the mixture, e.g., 4-10 weight % sodium tripolyphosphate by weight of the mixture.

3.16 Any of the foregoing methods, wherein the composition further comprises a fluoride ion source, e.g., a fluoride ion source selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

3.17 Method 3.16, wherein the fluoride ion source is present in an amount of 0.01-5 weight % by weight of the composition, e.g., 0.01-2 weight % by weight of the composition, e.g., 0.01-1 weight % by weight of the composition.

3.18 Any of the foregoing methods, wherein the composition further comprises another alkali phosphate salt.

3.19 Method 3.18, wherein the alkali phosphate salt is present in an amount of 1-10 weight % by weight of the composition.

3.20 Any of the foregoing methods, wherein the composition further comprises a humectant, e.g., a humectant selected from glycerin, sorbitol, propylene glycol, polyethylene glycol, xylitol, and combinations thereof.

3.21 Method 3.20, wherein the humectant is present in an amount of 2-50 weight % by weight of the composition, e.g., 10-40 weight % by weight of the composition, e.g., 15-30 weight % by weight of the composition.

3.22 Any of the foregoing methods, wherein the composition further comprises a surfactant, e.g., selected from anionic, cationic, zwitterionic, and nonionic surfactants, and combinations thereof, e.g., selected from sodium lauryl sulfate, sodium ether lauryl sulfate, cocamidopropylbetaine, a poloxamer, and combinations thereof.

3.23 Method 3.22, wherein the surfactant is present in an amount of 1-10 weight % by weight of the composition.

3.24 Any of the foregoing methods, wherein the composition further comprises a thickener, e.g., selected from a polysaccharide gums, e.g., xanthan gum and/or carrageenan, a silica thickener, a cellulosic polymer, e.g., sodium CMC, and combinations thereof.

3.25 Method 3.24, wherein the thickener is present in an amount of 1-10 weight % by weight of the composition.

3.26 Any of the foregoing methods, wherein the composition further comprises an abrasive, e.g., silica abrasive.

3.27 Method 3.26, wherein the abrasive is present in an amount of 10-30 weight % by weight of the composition.

3.28 Any of the foregoing methods, wherein the composition further comprises a pH agent to adjust the pH, e.g., selected from sodium bicarbonate, an alkali phosphate, sodium hydroxide, citric acid, sodium citrate, and combinations thereof.

3.29 Method 3.28, wherein the pH agent is present in an amount of 0.1-10 weight % by weight of the composition, e.g., 1-5 weight % by weight of the composition, e.g., 1-3 weight % by weight of the composition.

3.30 Any of the foregoing methods, wherein the composition further comprises flavoring, fragrance, and/or coloring.

3.31 Any of the foregoing methods, wherein the composition further comprises 2-90 weight % water by weight of the composition, e.g., 2-50 weight % water by weight of the composition, e.g., 50-80 weight % water by weight of the composition.

3.32 Any of the foregoing methods, wherein the composition further comprises more than 20 weight % water by weight of the composition, e.g., at least 30 weight % water by weight of the composition, e.g., at least 40 weight % water by weight of the composition, e.g., at least 50 weight % water by weight of the composition, e.g., at least 60 weight % water by weight of the composition, e.g., at least 70 weight % water by weight of the composition.

3.33 Any of the foregoing methods, wherein the composition comprises an aqueous solution.

3.34 Any of the foregoing methods, wherein the composition comprises tin (II) fluoride.

3.35 Any of Method 3a, 3b, or 3.1-3.33, wherein the composition comprises tin (II) chloride.

3.36 Method 3.34, wherein the composition has a pH from 4-9, e.g. from 5-8, e.g., from 5-7, e.g., from 5-6, e.g., from 6-8, e.g., from 6-7, e.g., from 7-8.

3.37 Method 3.35, wherein the composition has a pH from 4-9, e.g., from 4-8, e.g., from 4-7, e.g., from 5-8, e.g., from 6-8, e.g., from 5-7, e.g., from 4-6, e.g., from 4-5, e.g., from 5-6, e.g., from 6-7, e.g., from 7-8.

3.38 Any of the foregoing methods, wherein the composition is any of Composition 1 et seq.

3.39 Any of the foregoing methods, wherein the composition is a mouthwash, oral gel, or dentifrice, e.g., a mouthwash.

3.40 Any of the foregoing methods to reduce or inhibit dentinal hypersensitivity.

3.41 Any of the foregoing methods to reduce or inhibit dental caries.

3.42 Any of the foregoing methods to reduce or inhibit gingivitis.

3.43 Any of the foregoing methods to reduce or inhibit plaque.

3.44 Any of the foregoing methods to occlude dentin tubules.

Further provided is a method (Method 4) of making an oral care composition, e.g., any of Composition 1 et seq., comprising an aqueous soluble tin phosphate complex formed from a mixture comprising tin (II) fluoride or tin (II) chloride and a tripolyphosphate salt, e.g., an alkali tripolyphosphate salt, e.g., potassium tripolyphosphate ($K_5P_3O_{10}$) or sodium tripolyphosphate ($Na_5P_3O_{10}$), e.g., any of Complex 1 et seq., comprising combining the complex, e.g., any of Complex 1 et seq., with an oral care base, e.g., a mouthwash, oral gel, or dentifrice base, e.g., 4.1 Method 4, wherein the complex is formed in situ in the composition, e.g., wherein the composition has a pH from 4-9, e.g., from 5-8, e.g., from 5-7, e.g., from 5-6, e.g., from 6-8, e.g., from 6-7, e.g., from 7-8. For instance, wherein the complex is formed in situ in the composition from tin (II) fluoride and the tripolyphosphate salt, e.g., alkali tripolyphosphate salt, e.g., wherein the composition has a pH from 4-9, e.g., from 5-8, e.g., from 5-7, e.g., from 5-6, e.g., from 6-8, e.g., from 6-7, e.g., from 7-8. For instance, wherein the complex is formed in situ in the composition from tin (II) chloride and the tripolyphosphate salt, e.g., alkali tripolyphosphate salt, e.g., wherein the composition has a pH from 4-9, e.g., from 4-8, e.g., from 4-7, e.g., from 5-8, e.g., from 6-8, e.g., from 5-7, e.g., from 4-6, e.g., from 4-5, e.g., from 5-6, e.g., from 6-7, e.g., from 7-8.

4.2 Method 4, wherein the complex is formed in situ in an aqueous solution and combined with the oral care base, e.g., wherein the aqueous solution has a pH from 4-9, e.g., from 5-8, e.g., from 5-7, e.g., from 5-6, e.g., from 6-8, e.g., from 6-7, e.g., from 7-8. For instance, wherein the complex is formed in situ in an aqueous solution from tin (II) fluoride and the tripolyphosphate salt, e.g., alkali tripolyphosphate salt, e.g., wherein the aqueous solution has a pH from 4-9, e.g., from 5-8, e.g., from 5-7, e.g., from 5-6, e.g., from 6-8, e.g., from 6-7, e.g., from 7-8. For instance, wherein the complex is formed in situ in an aqueous solution from tin (II) chloride and the tripolyphosphate salt, e.g., alkali tripolyphosphate salt, e.g., wherein the aqueous solution has a pH from 4-9, e.g., from 4-8, e.g., from 4-7, e.g., from 5-8, e.g., from 6-8, e.g., from 5-7, e.g., from 4-6, e.g., from 4-5, e.g., from 5-6, e.g., from 6-7, e.g., from 7-8.

4.3 Method 4 or 4.2, wherein the complex is combined as a solid with the oral care base, e.g., wherein the complex is isolated from the aqueous solution in solid form and combined with the oral care base, e.g., mouthwash, oral gel, or dentifrice base, e.g., a mouthwash base.

4.4 Any of Method 4, 4.2, or 4.3, wherein the complex is lyophilized and combined the complex with an oral care base, e.g., mouthwash, oral gel, or dentifrice base, e.g., a mouthwash base.

4.5 Any of Method 4 or 4.2-4.4, wherein the complex is isolated with an anti-solvent, e.g., an organic solvent, e.g., ethanol, and combined with the oral care base, e.g., mouthwash, oral gel, or dentifrice base, e.g., a mouthwash base.

4.6 Any of the foregoing methods, wherein the complex is made as described in any of Method 2 et seq.

4.7 Any of the foregoing methods, wherein the complex is present in an amount of 2-30 weight % by weight of the composition 4.8 Any of the foregoing methods, wherein the tripolyphosphate salt is sodium tripolyphosphate.

4.9 Any of the foregoing methods, wherein the complex is made by mixing tin (II) fluoride or tin (II) chloride and the tripolyphosphate salt, e.g., alkali tripolyphosphate salt, in a molar ratio of 1P:1Sn to less than 15P:1Sn, e.g., greater than 1P:1Sn to less than 15P:1Sn, e.g., 2P:1Sn to less than 15P:1Sn, e.g., 2P:1Sn to 10P:1Sn, e.g., 3P:1Sn to 10P:1Sn, e.g., greater than 2P:1Sn to less than 10P:1Sn, e.g., 2P:1Sn to 5P:1Sn, e.g., greater than 2P:1Sn to 5P:1Sn, e.g., 3P:1Sn to 5P:1Sn, e.g., 2P:1Sn, e.g., 3P:1Sn, e.g., 5P:1Sn. For instance, comprising mixing tin (II) fluoride and the tripolyphosphate salt, e.g., alkali tripolyphosphate salt, in a molar ratio of 1P:1Sn to less than 15P:1Sn, e.g., greater than 1P:1Sn to less than 15P:1Sn, e.g., 2P:1Sn to less than 15P:1Sn, e.g., 2P:1Sn to 10P:1Sn, e.g., 2P:1Sn to 5P:1Sn, e.g., 2P:1Sn, e.g., 5P:1Sn. For instance, comprising mixing tin (II) chloride and the tripolyphosphate salt, e.g., alkali tripolyphosphate salt, in a molar ratio of 2P:1Sn to 10P:1Sn, e.g., 3P:1Sn to 10P:1Sn, e.g., greater than 2P:1Sn to less than 10P:1Sn, e.g., 2P:1Sn to 5P:1Sn, e.g., greater than 2P:1Sn to 5P:1Sn, e.g., 3P:1Sn to 5P:1Sn, e.g., 3P:1Sn, e.g., 5P:1Sn.

4.10 Any of the foregoing methods, wherein the complex is made by mixing tin (II) fluoride or tin (II) chloride and sodium tripolyphosphate in a molar ratio of 1P:1Sn to less than 15P:1Sn, e.g., greater than 1P:1Sn to less than 15P:1Sn, e.g., 2P:1Sn to less than 15P:1Sn, e.g., 2P:1Sn to 10P:1Sn, e.g., 3P:1Sn to 10P:1Sn, e.g., greater than 2P:1Sn to less than 10P:1Sn, e.g., 2P:1Sn to 5P:1Sn, e.g., greater than 2P:1Sn to 5P:1Sn, e.g., 3P:1Sn to 5P:1Sn, e.g., 2P:1Sn, e.g., 3P:1Sn, e.g., 5P:1Sn. For instance, comprising mixing tin (II) fluoride and sodium tripolyphosphate in a molar ratio of 1P:1Sn to less than 15P:1Sn, e.g., greater than 1P:1Sn to less than 15P:1Sn, e.g., 2P:1Sn to less than 15P:1Sn, e.g., 2P:1Sn to 10P:1Sn, e.g., 2P:1Sn to 5P:1Sn, e.g., 2P:1Sn, e.g., 5P:1Sn. For instance, comprising mixing tin (II) chloride and sodium tripolyphosphate in a molar ratio of 2P:1Sn to 10P:1Sn, e.g., 3P:1Sn to 10P:1Sn, e.g., greater than 2P:1Sn to less than 10P:1Sn, e.g., 2P:1Sn to 5P:1Sn, e.g., greater than 2P:1Sn to 5P:1Sn, e.g., 3P:1Sn to 5P:1Sn, e.g., 3P:1Sn, e.g., 5P:1Sn.

4.11 Method 4.10, wherein the complex is made by mixing tin (II) fluoride and sodium tripolyphosphate in a molar ratio of 2P:1Sn to 5P:1Sn, e.g., 2P:1Sn, e.g., 5P:1Sn.

4.12 Method 4.10, wherein the complex is made by mixing tin (II) chloride and sodium tripolyphosphate in a molar ratio of greater than 2P:1Sn to 5P:1Sn, e.g., 3P:1Sn to 5P: 1Sn, e.g., 3P:1Sn, e.g., 5P:1Sn.

4.13 Any of the foregoing methods, wherein the complex is made by mixing 1-10 weight % tin (II) fluoride or tin (II) chloride by weight of the mixture, e.g., 1-9 weight % tin (II) fluoride or tin (II) chloride by weight of the mixture, e.g., 3 weight % tin (II) fluoride or tin (II) chloride by weight of the mixture, e.g., 2 weight % tin (II) fluoride or tin (II) chloride by weight of the mixture, and 1-20 weight % tripolyphosphate salt, e.g., alkali tripolyphosphate salt, by weight of the mixture, e.g., 1-15 weight % tripolyphosphate salt by weight of the mixture, e.g., more than 3 weight % tripolyphosphate salt to less than 16 weight % tripolyphosphate salt by weight of the mixture, e.g., 4-15 weight % tripolyphosphate salt by weight of the mixture, e.g., 1-10 weight % tripolyphosphate salt by weight of the mixture, e.g., 4-10 weight % tripolyphosphate salt by weight of the mixture, e.g., 3-4 weight % tripolyphosphate salt by weight of the mixture, e.g., 7-8 weight % tripolyphosphate salt by weight of the mixture. For instance, comprising mixing 1-10 weight % tin (II) fluoride by weight of the mixture, e.g., 1-9 weight % tin (II) fluoride by weight of the mixture, e.g., 2 weight % tin (II) fluoride by weight of the mixture, and 1-10 weight % tripolyphosphate salt, e.g., alkali tripolyphosphate salt, by weight of the mixture, e.g., 3-4 weight % tripolyphosphate salt by weight of the mixture, e.g., 7-8 weight % tripolyphosphate salt by weight of the mixture. For instance, comprising mixing 1-10 weight % tin (II) chloride by weight of the mixture, e.g., 1-9 weight % tin (II) chloride by weight of the mixture, e.g., 3 weight % tin (II) chloride by weight of the mixture, and 1-20 weight % tripolyphosphate salt, e.g., alkali tripolyphosphate salt, by weight of the mixture, e.g., 1-15 weight % tripolyphosphate salt by weight of the mixture, e.g., more than 3 weight % tripolyphosphate salt to less than 16 weight % tripolyphosphate salt by weight of the mixture, e.g., 4-15 weight % tripolyphosphate salt by weight of the mixture, e.g., 1-10 weight % tripolyphosphate salt by weight of the mixture, e.g., 4-10 weight % tripolyphosphate salt by weight of the mixture.

4.14 Any of the foregoing methods, wherein the complex is made by mixing 1-10 weight % tin (II) fluoride or tin (II) chloride by weight of the mixture, e.g., 1-9 weight % tin (II) fluoride or tin (II) chloride by weight of the mixture, e.g., 3 weight % tin (II) fluoride or tin (II) chloride by weight of the mixture, e.g., 2 weight % tin (II) fluoride or tin (II) chloride by weight of the mixture, and 1-20 weight % sodium tripolyphosphte by weight of the mixture, e.g., 1-15 weight % sodium tripolyphosphte by weight of the mixture, e.g., more than 3 weight % sodium tripolyphosphate to less than 16 weight % sodium tripolyphosphate by weight of the mixture, e.g., 4-15 weight % sodium tripolyphosphate by weight of the mixture, e.g., 1-10 weight % sodium tripolyphosphate by weight of the mixture, e.g., 4-10 weight % sodium tripolyphosphate by weight of the mixture, e.g., 3-4 weight % sodium tripolyphosphate by weight of the mixture, e.g., 7-8 weight % sodium tripolyphosphate by weight of the mixture. For instance, comprising mixing 1-10 weight % tin (II) fluoride by weight of the mixture, e.g., 1-9 weight % tin (II) fluoride by weight of the mixture, e.g., 2 weight % tin (II) fluoride by weight of the mixture, and 1-10 weight % sodium tripolyphosphate by weight of the mixture, e.g., 3-4 weight % sodium tripolyphosphate by weight of the mixture, e.g., 7-8 weight % sodium tripolyphosphate by weight of the mixture. For instance, comprising mixing 1-10 weight % tin (II) chloride by weight of the mixture, e.g., 1-9 weight % tin (II) chloride by weight of the mixture, e.g., 3 weight % tin (II) chloride by weight of the mixture, and 1-20 weight % sodium tripolyphosphate by weight of the mixture, e.g., 1-15 weight % sodium tripolyphosphate by weight of the mixture, e.g., more than 3 weight % sodium tripolyphosphate to less than 16 weight % sodium tripolyphosphate by weight of the mixture, e.g., 4-15 weight % sodium tripolyphosphate salt by weight of the mixture, e.g., 1-10 weight % sodium tripolyphosphate by weight of the mixture, e.g., 4-10 weight % sodium tripolyphosphate salt by weight of the mixture. 4.15 Any of the foregoing methods, wherein the oral care base is a mouthwash base.

Tin (II) fluoride or tin (II) chloride and a tripolyphosphate salt, e.g., an alkali tripolyphosphate salt, e.g., sodium tripolyphosphate, may be combined to form a pre-formed aqueous soluble tin phosphate complex, e.g., any of Complex 1 et seq., which may be prepared in bulk, and then incorporated into the oral care compositions disclosed herein, e.g., any of Composition 1 et seq. Alternatively, tin (II) fluoride or tin (II) chloride and a tripolyphosphate salt, e.g., an alkali tripolyphosphate salt, e.g., sodium tripolyphosphate, may be combined during the manufacture of the oral care compositions disclosed herein, e.g., any of Composition 1 et seq., to form the complex in situ in the composition.

In some embodiments the oral care compositions disclosed herein, e.g., any of Composition 1 et seq., comprise one or more fluoride ion sources—i.e., a fluoride-containing compound having a beneficial effect on the care and hygiene of the oral cavity, for example, diminution of enamel solubility in acid and protection of the teeth against decay. Any suitable fluoride source may be employed including, without limitation, sodium fluoride, stannous fluoride, potassium fluoride, potassium stannous fluoride (SNFZ-KF), potassium fluorozirconate, sodium hexafluorostannate, stannous chlorofluoride, sodium monofluorophosphate (MFP), or a combination of two or more thereof. Where present, the fluoride source may provide fluoride ion in amounts sufficient to supply 25-25,000 ppm of fluoride ions, generally at least 500 ppm, e.g., 500-2000 ppm, e.g., 1000-1600 ppm, e.g., 1450 ppm. The appropriate level of fluoride will depend on the particular application. A toothpaste for general consumer use would typically have 1000-1500 ppm, e.g., 1100 ppm, e.g., 1000 ppm, with pediatric toothpaste having somewhat less. A dentifrice or coating for professional application could have as much as 5,000 or even 25,000 ppm fluoride. In some embodiments, the one or more further fluoride ion sources are present in the oral care compositions disclosed herein, e.g., Composition 1 et seq., in an amount of 0.01-5 weight % by weight of the composition, e.g., 0.01-2 weight % by weight of the composition, e.g., 0.01-1 weight % by weight of the composition.

In some embodiments, the oral care compositions disclosed herein, e.g., any of Composition 1 et seq., comprise one or more humectants. Any suitable humectant may be employed including, without limitation, polyhydric alcohols (polyols) such as propylene glycol, glycerin, sorbitol, xylitol, low molecular weight polyethylene glycols (PEGs), or a combination of two or more thereof. Humectants may, for example, prevent hardening of paste or gel compositions upon exposure to air. Certain humectants may also impart desirable sweetness of flavor to the compositions. In some embodiments, the one or more humectants are present in the oral care compositions disclosed herein, e.g., any of Composition 1 et seq., in an amount of 2-50 weight % by weight of the composition, e.g., 10-40 weight % by weight of the composition, e.g., 15-30 weight % by weight of the composition.

In some embodiments, the oral care compositions disclosed herein, e.g., any of Composition 1 et seq., comprise one or more surfactants. Any suitable surfactant may be employed including, without limitation, anionic, nonionic, and amphoteric surfactants. Surfactants may, for example, provide enhanced stability of the composition, to help in cleaning the oral cavity surfaces through detergency, and to increase foaming of the composition upon agitation, e.g., during brushing. Suitable anionic surfactants include, for example, water-soluble salts of $C_{8-20}$ alkyl sulfates, sulfonated monoglycerides of $C_{8-20}$ fatty acids, sarcosinates, taurates, or a combination of two or more thereof; for example sodium lauryl sulfate, sodium coconut monoglyceride sulfonate, sodium lauroyl sarcosinate, sodium lauroyl isoethionate, sodium laureth carboxylate, sodium dodecyl benzenesulfonate, or a combination of two or more thereof. In some embodiments, the one or more surfactants are present in the oral care compositions disclosed herein, e.g., Composition 1 et seq., in an amount of 1-10 weight % by weight of the composition.

In some embodiments, the oral care compositions disclosed herein, e.g., any of Composition 1 et seq., comprise one or more thickeners, which may impart a desired consistency and/or mouth feel to the composition. Any suitable thickener or binder may be employed including, without limitation, carbomers (also known as carboxyvinyl polymers), carrageenans (also known as Irish moss and more particularly 1-carrageenan (iota-carrageenan)), cellulosic polymers such as hydroxyethylcellulose, carboxymethylcellulose (CMC) and salts thereof, e.g., sodium CMC, natural gums such as gum karaya, xanthan gum, gum arabic, and gum tragacanth, inorganic thickeners such as colloidal magnesium aluminum silicate, colloidal silica, and the like, or a combination of two or more thereof. In some embodiments, the one or more thickeners are present in the oral care compositions disclosed herein, e.g., Composition 1 et seq., in an amount of 1-10 weight % by weight of the composition.

In some embodiments, the oral care compositions disclosed herein, e.g., any of Composition 1 et seq., comprise one or more flavorings. Any suitable flavoring, e.g., sweetening agent, may be employed including, without limitation, flavoring oils (e.g. oil of spearmint, peppermint, wintergreen, clove, sage, eucalyptus, marjoram, cinnamon, lemon, and orange), sucrose, sucralose, lactose, maltose, xylitol, stevia, sodium cyclamate, perillartine, aspartame, liquorice, saccharin or a salt thereof, or a combination of two or more thereof. In some embodiments, the one or more flavorings are present in the oral care compositions disclosed herein, e.g., any of Composition 1 et seq., in an amount of 0.01-10 weight % by weight of the composition, e.g., 0.05-5 weight % by weight of the composition, e.g., 0.05-0.2 weight % by weight of the composition, e.g., 1-3 weight % by weight of the composition.

In some embodiments, the oral care compositions disclosed herein, e.g., any of Composition 1 et seq., comprise one or more colorants. Any suitable colorant may be employed including, without limitation, zinc oxide, talc, titanium dioxide, pigments, dyes, or a combination of two or more thereof. In some embodiments, the colorant is a water soluble oral grade dye or colorant, including naturally-derived dyes (e.g., chlorophyll). In some embodiments, the oral care compositions disclosed herein, e.g., any of Composition 1 et seq., comprise the one or more colorants, in an amount of 0.01-5 weight % by weight of the composition, e.g., 0.05-2 weight % by weight of the composition.

In some embodiments, the oral care compositions disclosed herein, e.g., any of Composition 1 et seq., comprise water. Water employed in the preparation of commercial oral care compositions should be deionized and free of organic impurities. In some embodiments, water makes up the balance of the oral care compositions. In some embodiments, the oral care compositions disclosed herein, e.g., any of Composition 1 et seq., comprise water in an amount of 2-90 weight % by weight of the composition, e.g., 2-50 weight % by weight of the composition, e.g., 50-80 weight % by weight of the composition.

A complex disclosed herein may be described by reference to a spectrum as "substantially" shown or depicted in a figure or by one or more data points. It will be appreciated that a Fourier transform infrared, Raman, or NMR spectrum of a given sample may vary depending on factors known to those of skill in the art, e.g., instrument used, etc. Therefore, the Fourier transform infrared, Raman, and NMR spectrum peaks set forth herein will have an acceptable level of deviation. For example, for Fourier transform infrared spectra, the peaks may have an acceptable deviation of, e.g., $\pm 20$ $cm^{-1}$ or $\pm 16$ $cm^{-1}$ or $\pm 4$ $cm^{-1}$ or $\pm 2$ $cm^{-1}$ or $\pm 1$ $cm^{-1}$ or $\pm 0.5$ $cm^{-1}$. For example, for Raman spectra, the peaks may have an acceptable deviation of, e.g., $\pm 1$-$2$ $cm^{-1}$, e.g., $\pm 1$ $cm^{-1}$, e.g., $\pm 2$ $cm^{-1}$. For example, for NMR spectra, the peaks may have an acceptable deviation of, e.g., $\pm 1$ ppm.

As used herein, "aqueous solution" means a solution in which the solvent is water.

As used herein, "aqueous soluble tin phosphate complex" includes a complex in which 1 gram of the complex is soluble in 1 or 10 to 100 ml water, e.g., 1 or 10 to 90 ml water, e.g., 1 or 10 to 80 ml water, e.g., 1 or 10 to 70 ml water, e.g., 1 or 10 to 60 ml water, e.g., 1 or 10 to 50 ml water, e.g., 1 or 10 to 40 ml water, e.g., 1 or 10 to 30 ml water, e.g., 1 or 10 to 20 ml water, e.g., 1-10 ml water, e.g., less than 1 ml water.

EXAMPLES

Example 1

TABLE 1

Solution Preparation

| P:Sn Molar Ratio | Amount (g) | Percent in Solution | pH Upon Preparation |
|---|---|---|---|
| 0.2 | 0.4 $SnF_2$ | 2% $SnF2$ | 5.8 |
|  | 0.4 15% STPP solution | 2% STPP |  |
|  | 18.8 $H_2O$ | 96% $H_2O$ |  |
| 1 | 0.2 $SnF_2$ | 2% | 4.9 |
|  | 0.1 STPP | 2% |  |
|  | 7.6 $H_2O$ | 96% |  |
| 2 | 0.5 $SnF_2$ | 2% | 5.6 |
|  | 0.7 STPP | 3% |  |
|  | 22.3 $H_2O$ | 95% |  |
| 5 | 0.3 $SnF_2$ | 2% | 7.8 |
|  | 1.2 STPP | 8% |  |
|  | 14.1 $H_2O$ | 90% |  |
| 10 | 0.3 $SnF_2$ | 2% | 8.0 |
|  | 2.5 STPP | 16% |  |
|  | 12.9 $H_2O$ | 82% |  |
| 15 | 0.2 $SnF_2$ | 2% | Does not form a clear solution upon preparation |
|  | 1.8 STPP | 24% |  |
|  | 5.8 $H_2O$ | 74% |  |

Solutions are prepared by first dissolving sodium tripolyphosphate (STPP) in water (mixing under high heat if necessary) and then adding stannous fluoride ($SnF_2$) to the clear solution. The solutions are then further mixed at room temperature until a clear solution forms. All of the solutions contain 2% $SnF_2$. A clear solution forms for all of the solutions except for P:Sn=15 molar ratio.

The solutions with a P:Sn molar ratio spanning from 1 to 15 containing 2% SnF2 are aged overnight at room temperature. After overnight aging, only the solutions with a P:Sn molar ratio spanning from 2 to 10 remain clear.

After aging for two days, the solution with a P:Sn molar ratio of 10 contains a little precipitate on the bottom of the vial.

The solutions with a P:Sn molar ratio of 2 and 5 remain stable after aging for two weeks at room temperature.

A different set of solutions with a P:Sn molar ratio of 2 and 5 are placed in a 50° C. oven for eight weeks. After the aging period, the solutions appear clear.

A 2% stannous fluoride solution shows precipitate almost immediately after dissolution.

Example 2

TABLE 2

Preparation of 1% Bovine Serum Albumin (BSA) Solutions

| Sample | Amount of BSA (g) | Amount of Total Solution (g) |
|---|---|---|
| 1% BSA in 1Sn: 2P solution RT | 0.05 | 5 |
| 1% BSA in 1Sn: 5P solution RT | 0.05 | 5 |
| 1% BSA in 1Sn: 2P solution 37° C. | 0.05 | 5 |
| 1% BSA in 1Sn: 5P solution 37° C. | 0.05 | 5 |
| Control: 1% BSA in DI water | 0.02 | 2 |

Bovine serum albumin (BSA) is used to model interaction of solutions with oral proteins.

Aging of the BSA Solutions

The solutions with a P:Sn molar ratio of 2 and 5 containing 1% bovine serum albumin (BSA) are aged at 37° C. and at room temperature overnight.

Both solutions of stannous fluoride ($SnF_2$) and sodium tripolyphosphate (STPP) with 1% BSA form a precipitate after aging overnight at 37° C. The solution with a P:Sn molar ratio of 5 forms clumps of precipitates. The solution with a P:Sn molar ratio of 2 appears turbid throughout.

The solution with a P:Sn molar ratio of 2 with 1% BSA forms a precipitate after aging overnight at room temperature.

The solution with a P:Sn molar ratio of 5 with 1% BSA has a little precipitate after aging overnight at room temperature but still remains relatively clear.

A 1% BSA control after aging overnight at room temperature shows no precipitate. A 1% BSA control after aging overnight at 37° C. shows no precipitate.

Bovine serum albumin (BSA) stimulates proteins found in saliva. Formation of precipitate upon exposure to BSA may block dentin tubules to provide hypersensitivity relief.

Example 3

Compositions comprising elevated concentrations of a complex comprising tin (II) fluoride and a polyphosphate, having a P:Sn molar ratio of 2, are evaluated.

TABLE 3

Preparation of Solutions Containing a High Concentration of Stannous Fluoride

| P:Sn Molar Ratio | Amount (g) | Percent in Solution | |
|---|---|---|---|
| 2 | 0.2 $SnF_2$ | 9% | Solution remains clear |
|  | 1.6 STPP 15% STPP solution | 14% |  |
|  | — | 78% |  |
| 2 | 0.2 $SnF_2$ | 10% | Solution is clear upon preparation but becomes turbid overnight |
|  | 0.2 STPP | 16% |  |
|  | 1.2 $H_2O$ | 74% |  |
| 2 | 0.2 $SnF_2$ | 11% | Does not form a clear solution |
|  | 0.2 STPP | 18% |  |
|  | 1 $H_2O$ | 71% |  |

As illustrated by the data described in Table 3 (above), only the solution containing 9% $SnF_2$ remains clear after 1 week at room temperature.

Example 4

A clear solution comprising 2% stannous fluoride ($SnF_2$) and sodium tripolyphosphate (STPP) with a P:Sn molar ratio of 5 is lyophilized using a Labconco FreeZone 2.5 Freeze Dryer. FTIR-ATR analysis is conducted on freeze dried powder on an extended range Spectrum One Perkin Elmer system featuring a CsI beam splitter, DTGS detector, and single-bounce diamond KRS-5 ATR crystal. Sample is placed directly on the ATR diamond. See FIG. 1. Peaks observed for the Sn-STPP complex are listed in Table 4 (broad peaks from water/ethanol at about 1640 and 3200 $cm^{-1}$ are omitted from peak table).

TABLE 4

| Wavenumber ($cm^{-1}$) | Absorbance (A) |
| --- | --- |
| 512 | 0.9993 |
| 733 | 0.3144 |
| 883 | 0.6826 |
| 969 | 0.536 |
| 1081 | 0.4922 |

Figure 6:
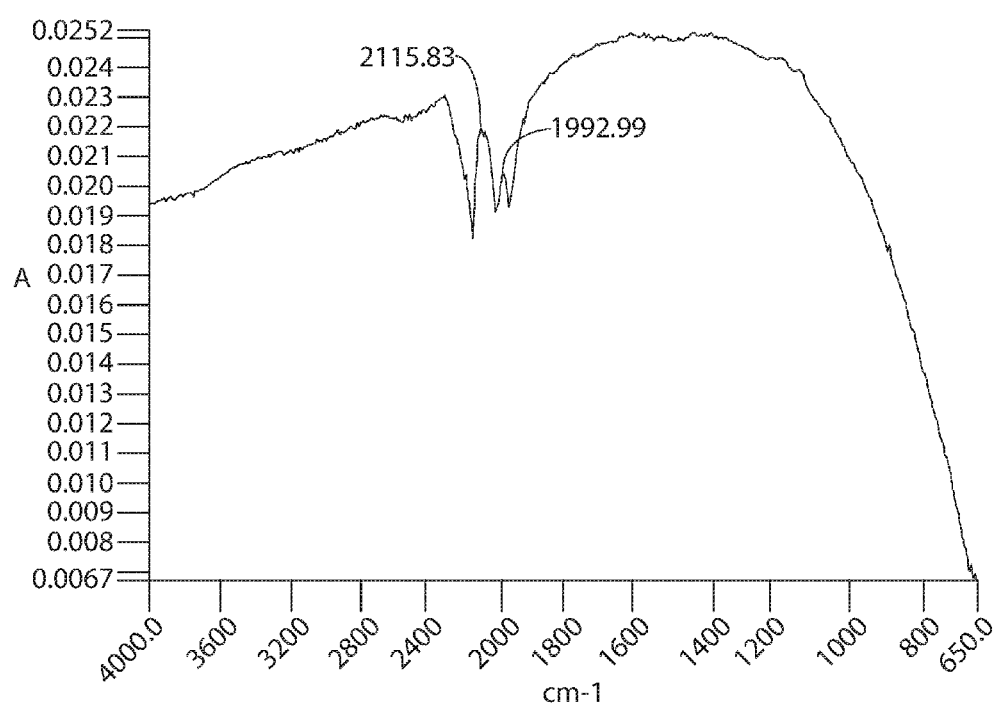
FIG. 6 is a Fourier transform infrared spectrum of $SnF_2$.

Ethanol is added dropwise to a clear solution comprising 2% stannous fluoride ($SnF_2$) and sodium tripolyphosphate (STPP) with a P:Sn molar ratio of 5 until precipitate forms. Solid is filtered and air dried. FTIR-ATR analysis is conducted on solid on an extended range Spectrum One Perkin Elmer system featuring a CsI beam splitter, DTGS detector, and single-bounce diamond KRS-5 ATR crystal. Sample is placed directly on the ATR diamond. See FIG. 2. An FTIR-ATR for solid $SnF_2$ is in FIG. 6.

FTIR-ATR analysis may be conducted on about 10-100 mg of solid.

Example 5

TABLE 5

| P:Sn Molar Ratio | Amount (g) | pH Upon Preparation |
| --- | --- | --- |
| 1 | 0.2 $SnCl_2 \cdot 2H_2O$<br>0.1 STPP<br>7.5 $H_2O$ | Turbid<br>1.6 |
| 2 | 0.2 $SnCl_2 \cdot 2H_2O$<br>1.6 15% STPP solution<br>6.0 $H_2O$ | Turbid<br>3.2 |
| 3 | 0.2 $SnCl_2 \cdot 2H_2O$<br>2.5 15% STPP solution<br>5.2 $H_2O$ | Clear<br>4.4 |
| 5 | 0.2 $SnCl_2 \cdot 2H_2O$<br>4.1 15% STPP solution<br>3.5 $H_2O$ | Clear<br>7.1 |
| 10 | 0.2 $SnCl_2 \cdot 2H_2O$<br>1.2 STPP<br>6.4 $H_2O$ | Cloudy<br>7.7 |
| 15 | 0.2 $SnCl_2 \cdot 2H_2O$<br>1.8 STPP<br>5.8 $H_2O$ | Turbid<br>7.4 |

Upon preparation, the solutions with P/Sn molar ratios of 1, 2, and 15 appear turbid and the solution with a P/Sn molar ratio of 10 appears slightly cloudy. Only the solutions with P/Sn molar ratios of 3 and 5 are clear.

The solutions are aged overnight at room temperature. After 24 hours, the solutions containing a P/Sn molar ratio of 3 and 5 remain clear. The solutions with P/Sn molar ratios of 1, 2, and 15 are turbid and the solution with a P/Sn molar ratio of 10 appears slightly cloudy.

Example 6

Solutions of 2% $SnF_2$ and STPP in water with P/Sn molar ratios of 2, 5, and 10 are prepared. The solutions are analyzed as-prepared on an Agiltron PeakSeeker Raman System equipped with a fiber optic probe designed for liquid samples. The spectra, obtained in 30 second integration times, is compared to that of scintillation vials containing deionized water as a blank using RSIQ software. Raman spectra for the solutions are shown in FIG. 3 and peaks are listed in Table 6 (below).

TABLE 6

| Sample | Raman Shift ($cm^{-1}$) |
| --- | --- |
| STPP | 705<br>978<br>1022<br>1094 |
| P/Sn 2 | 719<br>1084 |
| P/Sn 5 | 719<br>978<br>1094 |
| P/Sn 10 | 712<br>978<br>1094 |

Example 7

Figure 7:
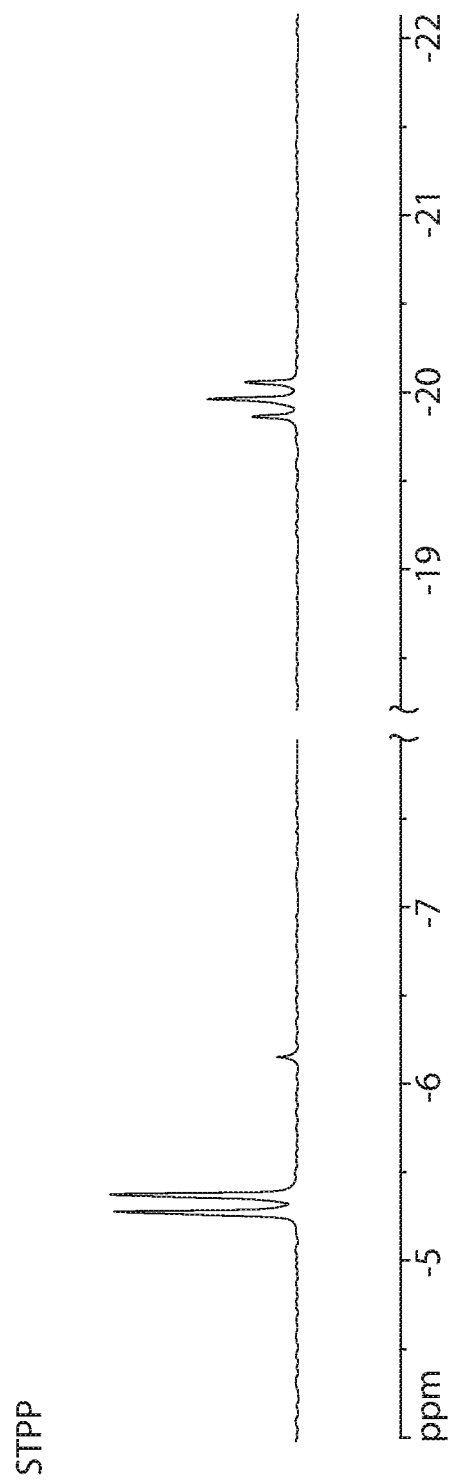
FIG. 7 depicts a $^{31}P$ NMR spectrum of a solution of STPP.

Solutions of 2% $SnF_2$ and STPP in water with P/Sn molar ratios of 2, 5, and 10 are prepared. 5 weight % $D_2O$ is added to the solutions. $^{31}P$ and $^{119}Sn$ NMR are acquired on a Bruker AVANCE 500 spectrometer working at 202.4 MHz for $^{31}P$ NMR and 163.5 MHz for $^{119}Sn$ NMR at room temperature. $^{31}P$ NMR are externally referenced to 85% $H_3PO_4$ set to 0 ppm. $^{119}Sn$ NMR are externally referenced to saturated $SnF_2$ in $D_2O$ at −796 ppm prepared right before measurement. FIGS. 4, A, 4, B, and 4, C depict $^{31}P$ NMR spectra of solutions with P:Sn molar ratios of 10 (FIG. 4, A), 5 (FIG. 4, B), and 2 (FIG. 4, C). FIGS. 5, A, 5, B, and 5, C depict $^{119}Sn$ NMR spectra of solutions with P:Sn molar ratios of 10 (FIG. 5, A), 5 (FIG. 5, B), and 2 (FIG. 5, C). $^{31}P$ NMR peaks are listed in Table 7 and $^{119}Sn$ NMR peaks are listed in Table 8. A $^{31}P$ NMR spectrum of a solution of STPP in water with 5 weight % $D_2O$ added and externally referenced to 85% $H_3PO_4$ set to 0 ppm is in FIG. 7.

TABLE 7

| | P/Sn Molar Ratio | $^{31}P$ Chemical Shift (ppm) |
| --- | --- | --- |
| $SnF_2$-STPP | 10 | 2.21<br>−6.24 (doublet)<br>−6.33 (doublet)<br>−6.68<br>−19.08 (triplet)<br>−19.17 (triplet)<br>−19.27 (triplet) |
| $SnF_2$-STPP | 5 | 1.73<br>−7.27<br>−7.52 (doublet)<br>−7.62 (doublet)<br>−9.89<br>−10.37<br>−10.83 |

TABLE 7-continued

| | P/Sn Molar Ratio | $^{31}$P Chemical Shift (ppm) |
|---|---|---|
| | | −11.62 |
| | | −19.09 (triplet) |
| | | −19.19 (triplet) |
| | | −19.29 (triplet) |
| SnF$_2$-STPP | 2 | −8.27 (doublet) |
| | | −8.37 (doublet) |
| | | −9.07 |
| | | −17.69 (triplet) |
| | | −17.79 (triplet) |
| | | −17.89 (triplet) |

TABLE 8

| | P/Sn Molar Ratio | $^{119}$Sn Chemical Shift (ppm) |
|---|---|---|
| SnF$_2$-STPP | 10 | −687.87 |
| SnF$_2$-STPP | 5 | −684.61 |
| | | −691.73 |
| | | −699.51 |
| | | −714.30 |
| | | −717.32 |
| | | −723.01 |
| | | −725.28 |
| | | −732.59 |
| SnF$_2$-STPP | 2 | −714.97 |

Example 8

A toothpaste comprising the aqueous soluble tin phosphate complex as disclosed herein can be formulated as described in Table 9 below:

TABLE 9

| Material | Weight Percent |
|---|---|
| Aqueous soluble tin phosphate complex | 2-30% |
| Water | 2-50% |
| Alkali phosphate(s) | 1-10%, e.g., 5% |
| pH Agent(s) | 1-5%, e.g., 3% |
| Abrasive(s) | 10-30%, e.g., 20% |
| Thickener(s) | 1-5%, e.g., 3% |
| Surfactant(s) | 1-5%, e.g., 3% |
| Humectant(s) | 2-50% |
| Flavoring(s) | 1-5%, e.g., 3% |
| Coloring(s) | 0.1-2%, e.g., 1% |

Example 9

A mouthwash comprising the aqueous soluble tin phosphate complex as disclosed herein can be formulated as described in Table 10 below:

TABLE 10

| Material | Weight Percent |
|---|---|
| Aqueous soluble tin phosphate complex | 2-30% |
| Fluoride ion source(s) | 0.01-1%, e.g., 0.05% |
| Flavoring(s) | 0.005-0.5%, e.g., 0.1-0.15% |
| Humectant(s) | 10-30%, e.g., 20% |
| Surfactant(s) | 0.1-1%, e.g., 0.4% |
| Water | 50-80% |

What is claimed is:

1. An oral care composition comprising an aqueous soluble tin phosphate complex formed from a mixture comprising tin (II) fluoride or tin (II) chloride and a tripolyphosphate salt; wherein the complex is formed in situ in an aqueous solution and combined with the composition; or is isolated from the aqueous solution in solid form and combined with the composition; or is lyophilized and combined with the composition; or is isolated with an anti-solvent and combined with the composition.

2. The composition of claim 1, wherein the tripolyphosphate salt is sodium tripolyphosphate (Na$_5$P$_3$O$_{10}$).

3. The composition of claim 1, wherein the complex is formed in situ in an aqueous solution and combined with the composition.

4. The composition of claim 3, wherein the complex is isolated from the aqueous solution in solid form and combined with the composition.

5. The composition of claim 1, wherein the complex is lyophilized and combined with the composition.

6. The composition of claim 1, wherein the complex is isolated with an anti-solvent and combined with the composition.

7. The composition of claim 1, wherein the complex is present in an amount of 2 to 30 weight % by weight of the composition.

8. The composition of claim 1, wherein the complex is formed from tin (II) fluoride or tin (II) chloride and the tripolyphosphate salt in a molar ratio of 1P:1Sn to less than 15P:1Sn.

9. The composition of claim 1, wherein the complex is formed from tin (II) fluoride or tin (II) chloride and the tripolyphosphate salt in a molar ratio of greater than 2P:1Sn to less than 10P:1Sn.

10. The composition of claim 1, wherein the complex is formed from tin (II) fluoride or tin (II) chloride and the tripolyphosphate salt in a molar ratio of 2P:1Sn to 5P:1Sn.

11. The composition of claim 1, wherein the complex is formed from tin (II) fluoride or tin (II) chloride and the tripolyphosphate salt in a molar ratio of 3P:1Sn to 5P:1Sn.

12. The composition of claim 1, wherein the complex is formed from tin (II) fluoride or tin (II) chloride and the tripolyphosphate salt in a molar ratio of 5P:1Sn.

13. The composition of claim 1, wherein the complex is formed from tin (II) fluoride or tin (II) chloride and sodium tripolyphosphate in a molar ratio of 1P:1Sn to less than 15P:1Sn.

14. The composition of claim 1, wherein the complex is formed from tin (II) fluoride or tin (II) chloride and sodium tripolyphosphate in a molar ratio of greater than 2P:1Sn to less than 10P:1Sn.

15. The composition of claim 1, wherein the complex is formed from tin (II) fluoride or tin (II) chloride and sodium tripolyphosphate in a molar ratio of 2P:1Sn to 5P:1Sn.

16. The composition of claim 1, wherein the complex is formed from tin (II) fluoride or tin (II) chloride and sodium tripolyphosphate in a molar ratio of 3P:1Sn to 5P:1Sn.

17. The composition of claim 1, wherein the complex is formed from tin (II) fluoride or tin (II) chloride and sodium tripolyphosphate in a molar ratio of 5P:1Sn.

18. The composition of claim 1, wherein the complex is formed from a mixture comprising 1 to 10 weight % tin (II) fluoride or tin (II) chloride by weight of the mixture and 1 to 20 weight % tripolyphosphate salt by weight of the mixture.

19. The composition of claim 1, wherein the complex is formed from a mixture comprising 1 to 10 weight % tin (II) fluoride or tin (II) chloride by weight of the mixture and 1 to 10 weight % tripolyphosphate salt by weight of the mixture.

20. The composition of claim 1, wherein the complex is formed from a mixture comprising 1 to 10 weight % tin (II) fluoride or tin (II) chloride by weight of the mixture and 1 to 20 weight % sodium tripolyphosphate by weight of the mixture.

21. The composition of claim 1, wherein the complex is formed from a mixture comprising 1 to 10 weight % tin (II) fluoride or tin (II) chloride by weight of the mixture and 1 to 10 weight % sodium tripolyphosphate by weight of the mixture.

22. The composition of claim 1, wherein the composition comprises tin (II) fluoride.

23. The composition of claim 1, wherein the composition comprises tin (II) chloride.

24. The composition of claim 1, wherein the composition comprises an aqueous solution.

25. The composition of claim 1 further comprising more than 20 weight % water by weight of the composition.

26. The composition of claim 1, wherein the composition is a mouthwash.

27. The composition of claim 1 for use to reduce dentinal hypersensitivity.

28. A method to reduce or inhibit dentinal hypersensitivity, dental caries, gingivitis, or plaque in a person in need thereof comprising applying an effective amount of an oral care composition as claimed in claim 1 to teeth of the person.

* * * * *